(12) United States Patent
Kim et al.

(10) Patent No.: US 7,009,053 B2
(45) Date of Patent: Mar. 7, 2006

(54) QUINOLINE DERIVATIVES AS CASPASE-3 INHIBITOR, PREPARATION FOR PRODUCING THE SAME AND PHARMACEUTICAL COMPOSITION COMPRISING THE SAME

(75) Inventors: Sung-Gyu Kim, Daejeon (KR); Yoon Sung Jung, Gyeonggi-do (KR); Jae Yang Kong, Daejeon (KR); Woo Kyu Park, Chungcheongbuk-do (KR)

(73) Assignees: Yungjin Pharmaceuticals Co., Ltd., Seoul (KR); Korea Research Institute of Chemical Technology, Daejeon (KR)

( * ) Notice: Subject to any disclaimer, the term of this patent is extended or adjusted under 35 U.S.C. 154(b) by 0 days.

(21) Appl. No.: 10/493,706

(22) PCT Filed: Apr. 30, 2003

(86) PCT No.: PCT/KR03/00875

§ 371 (c)(1),
(2), (4) Date: Apr. 16, 2004

(87) PCT Pub. No.: WO03/093240

PCT Pub. Date: Nov. 13, 2003

(65) Prior Publication Data

US 2004/0260094 A1    Dec. 23, 2004

(30) Foreign Application Priority Data

Apr. 30, 2002 (KR) ................ 10-2002-0023838

(51) Int. Cl.
C07D 215/38    (2006.01)
C07D 215/44    (2006.01)
A61K 31/47     (2006.01)

(52) U.S. Cl. .................. 546/159; 546/160; 514/312
(58) Field of Classification Search ............. 546/159, 546/160; 514/312
See application file for complete search history.

(56) References Cited

U.S. PATENT DOCUMENTS

| | | | |
|---|---|---|---|
| 5,082,841 A * | 1/1992 | Brown et al. ............ | 514/235.2 |
| 5,585,357 A | 12/1996 | Dolle et al. | |
| 6,153,591 A | 11/2000 | Cai et al. | |
| 6,355,618 B1 | 3/2002 | Cai et al. | |

FOREIGN PATENT DOCUMENTS

| | | |
|---|---|---|
| EP | 0 416 749 * | 3/1991 |
| WO | WO 93/05071 | 3/1993 |
| WO | WO 96/03982 | 2/1996 |
| WO | WO 99/06367 | 2/1999 |
| WO | WO 99/65451 | 12/1999 |
| WO | WO 00/32620 | 6/2000 |
| WO | WO 00/55157 | 9/2000 |
| WO | WO 02/085899 A1 | 10/2002 |
| WO | WO 02/092076 A1 | 11/2002 |

OTHER PUBLICATIONS

Gervais, F. G., et al., Involvement of Caspases in Proteolytic Cleavage of Alzheimer's Amyloid-β Precursor Protein and Amyloidogenic Aβ Peptide Formation, Cell, vol. 97, 395-406, Apr. 30, 1999.

(Continued)

Primary Examiner—D. Margaret Seaman
(74) Attorney, Agent, or Firm—Lucas & Mercanti, LLP

(57) ABSTRACT

The present invention relates to new quinoline derivatives of formula (1) or their pharmaceutically acceptable salts with caspase-3 inhibitory activity and their preparation methods, wherein $R_2$ is H; halogen; $C_{1-6}$alkyl; $C_{1-6}$ alkoxy; $C_{1-6}$ alkoxyalkyl; or $C_{3-6}$cycloalkyl; $R_1$ is formula (a); —CN; or formula (b); R is H; $C_{6-14}$aryl unsubstituted or substituted by halogen, $C_{1-6}$ alkyl, $C_{1-6}$ alkoxy or amino; 5–15 membered heterocyclic group unsubstituted or substituted by halogen, $C_{1-6}$ alkyl, $C_{1-6}$ alkoxy or amino; or —$(CH_2)_n$—$CHR_4R_5$. The present invention relates to a pharmaceutical composition for treating caspase-associated diseases by inhibiting the activity of caspase-3 which comprises the compound of formula (1) or its pharmaceutically acceptable salt.

12 Claims, No Drawings

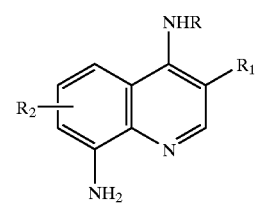

(I)

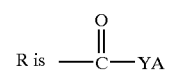

(II)

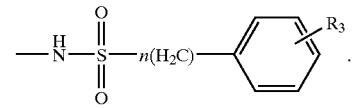

(III)

OTHER PUBLICATIONS

Walter, J., et al., Phosphorylation of Presenilin-2 Regulates its Cleavage by Caspases and Retards Progression of Apoptosis, Proc. Natl. Acad. Sci. USA, vol. 96, pp. 1391-1396, Feb. 1999.

Barnes, N. Y., et al., Increased Production of Amyloid Precursor Protein Provides a Substrate for Caspase-3 in Dying Motoneurons, J. Neuroscience, vol. 18(15), pp. 5869-5880, Aug. 1, 1998.

Kim, T. W., et al., Alternative Cleavage of Alzheimer-Associated Presenilins During Apoptosis by a Caspase-3 Family Protease, Science vol. 277(5324), pp. 373-376, Jul. 18, 1997.

Goldberg, Y. P., et al., Cleavage of Huntingtin by Apopain, a Proapoptotic Cysteine Protease, is Modulated by the Polyglutamine Tract, Nature Genetics, vol. 13(4), Aug. 13, 1996.

Wellington, C. L., et al., Caspase Cleavage of Gene Products Associated With Triplet Expansion Disorders Generates Truncated Fragments Containing the Polyglutamine Tract, J. Biol. Chem, vol. 273, No. 15, pp. 9158-9167, Apr. 10, 1998.

Sanchez, I., et al, Caspase-8 is Required for Cell Death Induced by Expanded Polyglutamine Repeats, Neuron, vol. 22(3)., pp. 623-633, Mar., 1999.

Dodel, R. C., et al., Caspase-3-Like Proteases and 6-Hydroxydopamine Induced Neuronal Cell Death, Mol. Brain Research, vol. 64(1), pp. 141-148, (1999).

Takai, N., et al., Involvement of Caspase-Like Proteinases in Apoptosis of Neuronal PC12 Cells and Primary Cultured Microglia Induced by 6-Hydroxydopamine, J. of Neurosci. Res. ,vol. 54(2), pp. 214-222 (1998).

Pasinelli, P., et al., Caspase-1 is Activated in Neural Cells and Tissue With Amyotrophic Lateral Sclerosis-Associated Mutations in Copper-Zinc Superoxide Dismutase, Proc. Natl. Acad. Sci. USA, vol. 95(26), pp. 15763-15768, Dec. 1998.

Kruman, I. I., et al., HIV-1 Protein TAT Induces Apoptosis of Hippocampal Neurons by a Mechanism Involving Caspase Activation, Calcium Overload, and Oxidative Stress, Exp. Neurol.., vol. 154(2), pp. 276-288, (1998).

Hara, H., et al., Inhibition of Interleukin 1β Converting Enzyme Family Proteases Reduces Ischemic and Excitotoxic Neuronal Damage, Proc. Natl. Acad. Sci. USA, vol. 94(5), pp. 2007-2012, Mar. 1997.

Namura S., et al., Activation and Cleavage of Caspase-3 in Apoptosis Induced by Experimental Cerebral Ischemia, J. Neurosci., vol. 18(10), pp. 3659-3668, May 15, 1998.

Schulz, J. B., et al., Caspases as Treatment Targets in Stroke and Neurodegenerative Diseases, Ann. Neurol., vol., 45 (4), pp. 421-429, Apr. 1999.

Yakovlev, A. G., et al., Activation of CPP32-Like Caspases Contributes to Neuronal Apoptosis and Neurological Dysfunction After Traumatic Brain Injury, J. Neurosci., vol. 17(19), pp. 7415-7424, Oct. 1, 1997.

Kermer, P., et al., Inhibition of CPP32-Like Proteases Rescues Axotomized Retinal Ganglion Cells From Secondary Cell Death in Vivo, J. Neurosci., vol. 18(12), pp. 4656-4662, Jun. 15, 1998.

Chaudhary, P., et al., Caspase Inhibitors Block the Retinal Ganglion Cell Death Following Optic Nerve Transection, Mol. Brain. Res., vol. 67, pp. 36-45, (1999).

Crowe, M. J., et al., Apoptosis and Delayed Degeneration After Spinal Cord Injury in Rats and Monkeys, Nat. Med., vol. 3(1), Jan. 1997.

Shuman, S. L., et al., Apoptosis of Microglia and Oligodendrocytes After Spinal Cord Contusion in Rats, J. Neurosci. Res., vol. 50(5), pp. 798-808, (1997).

* cited by examiner

QUINOLINE DERIVATIVES AS CASPASE-3 INHIBITOR, PREPARATION FOR PRODUCING THE SAME AND PHARMACEUTICAL COMPOSITION COMPRISING THE SAME

This patent application claims the benefit of priority from Korean Patent Application No. 10-2002-0023838 filed Apr. 30, 2002 through PCT Application Serial No. PCT/KR03/00875 filed Apr. 30, 2003, the contents of each of which are incorporated herein by reference.

FIELD OF THE INVENTION

The present invention relates to caspase-3 inhibitors. Specifically, the present invention relates to novel quinoline derivatives or their pharmaceutically acceptable salts as caspase-3 inhibitors, their preparation methods and pharmaceutical compositions comprising the same.

BACKGROUND OF THE INVENTION

Control of cell numbers in mammals is believed to be determined, in part, by a balance between cell proliferation and cell death. One form of cell death, sometimes referred to as necrotic cell death, is typically characterized by a pathologic form of cell death resulting from some trauma or cellular injury. Necrotic cell death is harmful to tissues, inducing inflammation and etc. In contrast, another "physiologic" form of cell death usually proceeds in an orderly or controlled manner. This orderly or controlled form of cell death is often referred to as "apoptosis" (Barr, et al., Bio/Technology, 12:487–497, 1994; Steller, et al., 267:1445–1449, 1995). Apoptosis is a programmed cell death by which orgamisms eliminate unwanted cells such as cells whose activity or existence is no longer required without damages to other tissues, thus eliminating damaged or excessive cells. Thus, apoptosis is a fundamentally important physiological process that is required to maintain normal development and homeostasis of an organism.

There are many factors which induce apoptosis. Amonog them, the most important protein is caspase of which 14 kinds are known. Capases are cystein protease enzymes and many important proteins in cells are used as substates for them. The process of apoptosis includes the steps that cells fragmented by caspase family enzymes are uptaken by other cells in small particle form, or eliminated by cells such as marcrophages without accompanying phenomena such as inflammation.

Caspases are classfied into two groups of initiator caspase and effector caspase. The initiator caspase receives the signal of apoptosis and transfers the signal to the effector caspase, and is represented by caspase-8, 9 and etc.

The effector caspase is directly involved in the apoptotic pathway to eliminate various cellular components and is represented by caspase-3, 6, 7 and etc. Among the effector caspases, caspase-3 has been well studied and functions as a final receptor in the apoptotic signal trasduction cascade. It has been shown in many studies that apoptosis can be prevented by inhibiting the expression or activity of caspase-3

Caspase-3 is a 32 kDa cystein protease and an effector caspase which plays an important role during morphogenetic cell death in a mammalian brain. The typical disease induced by the trouble in the apoptotic pathway in which caspases are involved is cancer. Cancer is one of diseases characterized by the failure to undergo apoptosis.

In contrast, the development of continuous apoptosis causes various neurological disorders. Representative diseases mediated by caspase-3 include Alzheimer's disease (Gervais F. G. et al., Cell, 97(3):395–406, 1999; Walter J. et al., Proc Natl Acad Sci USA 96(4):1391–6, 1999; Barnes N. Y. et al., J Neurosci 18(15):5869–80, 1998; Kim T. W. et al., Science 277(5324):373–6, 1997), Huntington's disease (Goldberg Y. P. et al., Nat Genet. 13(4):442–9, 1996; Wellington C. L. et al., J Biol Chem. 273(15):9158–67, 1998; Sanchez I. et al., Neuron. 22(3):623–33, 1999), Parkinson's disease (Dodel R. C. et al., Mol Brain Res 64(1):141–8, 1999; Takai N. et al., J Neurosci Res 54(2):214–22, 1998), ALS (amyltrophic lateral sclerosis) (Pasinelli P. et al., Proc Natl Acad Sci USA. 95(26):15763–8, 1998), AIDS (Kruman I. I. et al., Exp Neurol. 154(2):276–88, 1998), stroke/ischemia (Hara H. et al., Proc Natl Acad Sci USA. 94(5): 2007–12, 1997; Namura S. et al., J Neurosci. 18(10):3659–68, 1998; Schulz J. B. et al., Ann Neurol. 45(4):421–9, 1999), traumatic brain injury (Yakovlev A. G. et al., J Neurosci. 17(19):7415–24, 1997; Kermer P. et al., J Neurosci. 18(12):4656–62, 1998; Chaudhary P. et al, Mol Brain Res. 67(1):36–45, 1999), spinal cord injury (Crowe M. J. et al., Nat Med. 3(1):73–6, 1997; Shuman S. L. et al., J Neurosci Res. 50(5):798–808, 1997), osteoarthritis and etc.

Thus, there are many efforts to develop drugs effective against caspase-mediated diseases such as Alzheimer's disease, Huntington's disease, Parkinson's disease, ALS, AIDS, stroke/ischemia, traumatic brain injury, spinal cord injury, osteoarthritis and etc. as described in the above by using caspase-3 inhibitors.

Up to now, aspartic acids, peptide compounds, gamma-keto acids have been reported as caspase-3 inhibitors (WO93/05071, WO96.03982, U.S. Pat. No. 5,585,357, WO00/32620, WO00/55157, U.S. Pat. No. 6,153,591)

However, quinoline compounds have not been previously identified as caspase-3 inhibitors.

Under these circumstances, the inventors of this application completed the present invention by developing quinoline derivatives and their pharmaceutically acceptable salts, which have superior inhibitory activity against caspase-3

SUMMARY OF THE INVENTION

Therefore, the object of this invention is to provide novel quinoline derivatives of formula 1 or their pharmaceutically acceptable salts with caspase-3 inhibitory activity.

Another object of this invention is to provide methods for the preparation of the novel quinoline derivatives or their pharmaceutically acceptable salts.

A further object of this invention is to provide pharmaceutical compositions for the treatment of caspase-associated diseases comprising the novel quinoline derivatives or their pharmaceutically acceptable salts.

DETAILED DESCRIPTION OF THE INVENTION

The present invention relates to a quinoline derivative of formula 1 or its pharmaceutically acceptable salt:

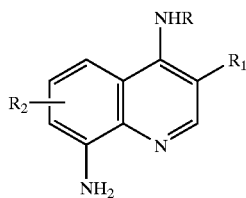

Formula 1 wherein

R₂ is H; halogen; $C_{1-6}$ alkyl; $C_{1-6}$ alkoxy; $C_{1-6}$ alkoxyalkyl; or $C_{3-6}$ cycloalkyl;

R₁ is

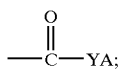

—CN; or

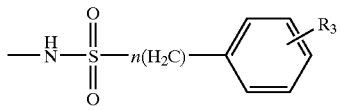

[wherein Y is O; N; or S;

A is H; $C_{3-6}$ alkenyl unsubstituted or substituted by $C_{1-3}$ alkyl; $C_{3-6}$ cycloalkyl; $C_{6-14}$ aryl unsubstituted or substituted by halogen, $C_{1-6}$ alkyl or $C_{1-6}$ alkoxy; $C_{1-6}$ alkoxyalkyl; or $C_{1-6}$ alkyl unsubstituted or substituted by $C_{6-14}$ aryl or 5–15 membered heteroaryl (wherein aryl group can be unsubstituted or substituted by halogen, $C_{1-6}$ alkyl, $C_{1-6}$ halogenoalkyl, $C_{1-6}$ alkoxy or amino group);

R₃ is H; halogen; unsubstituted or substituted amino; $C_{1-6}$ alkyl; $C_{1-6}$ alkoxy; $C_{1-6}$ alkoxyalkyl; or $C_{3-6}$ cycloalkyl;

n is 0, 1, 2 or 3];

R is H; $C_{6-14}$ aryl unsubstitued or substituted by halogen, $C_{1-6}$ alkyl, $C_{1-6}$ alkoxy or amino; 5–15 membered heterocyclic group unsubstituted or substituted by halogen, $C_{1-6}$ alkyl, $C_{1-6}$ alkoxy or amino; or —$(CH_2)_n$—$CHR_4R_5$ (wherein n is 0, 1, 2, 3 or 4;

R₄ is H; $C_{1-6}$ alkyl; $C_{1-6}$ alkoxy; $C_{6-14}$ aryl unsubstitued or substituted by halogen, $C_{1-6}$ alkyl, $C_{1-6}$ halogenoalkyl, $C_{1-6}$ alkoxy or amino; 5–15 membered heteroaryl; $C_{3-6}$ cycloalkyl; 5–15 membered heterocyclic group unsubstituted or substituted by $C_{1-6}$ alkyl; or 5–15 membered $C_{6-14}$ aryl fused to heterocyclic group;

R₅ is H; $C_{1-6}$ alkyl; $C_{1-6}$ alkoxy; or $C_{1-6}$ alkoxyalkyl).

The term "halogen" used in the specification means the atoms such as chlorine, fluorine, bromine and etc.

The term "alkyl" used herein means C1–C6 straight or branched saturated hydrocarbon groups, including methyl, ethyl, n-propyl, iso-propyl, n-butyl, sec-butyl, iso-butyl, tert-butyl and etc.

The term "halogenoalkyl" means alkyl groups wherein a hydrogen(s) of the alkyl group is substituted by halogen atom(s).

The term "alkoxy" means a group wherein C1–C6 straight or branched alkyl group is connected to oxygen, including methoxy, ethoxy, propoxy, isopropoxy, butoxy, isobutoxy and etc.

The term "alkoxyalkyl" means a alkyl radical wherein a hydrogen(s) of the alkyl group is substituted by alkoxy group(s) in which the alkoxy group can be straight or branched.

The term "cycloalkyl" means a C3–C6 non-aromatic hydrocarbon ring radical, including cyclopropyl, cyclobutyl, cyclopenty, cyclohexyl and etc.

The term "alkenyl" means a unsaturated hydrocarbon which is straight or branched, having one or more double bonds and 3–6 carbon atoms. The alkenyl radical can be unsubstituted or substituted by $C_{1-3}$ alkyl and etc.

The term "aryl" means a C1–C14 mono- or poly-cyclic aromatic ring, including phenyl, napthyl and etc. The aryl can be unsubstittued or have one or more substituent groups wherein the substituent group can include halogen, $C_{1-6}$ alkyl, $C_{1-6}$ halogenoalkyl, $C_{1-6}$ alkoxy, amino group and etc.

The term "heteroaryl" means a 5–15 membered aromatic radical which has one or more heteroatoms selected from O, N or S, preferably 1 or 2 heteroatoms which are the same or different, including pyrol, pyrozol, furan, thiopen, quinoline, isoquinoline, quinazolinyl, pyridine, pyrimidine, pyrazine, pyridazine, oxazole, oxadiazole, tetrazole, thiazole, thiadiazole, imidazole, benzimidazole, benzothiapen, benzopyrol, benzofuran and etc, perferably thiopen, pyridine and etc.

The term "heterocyclic" is a 5–15 membered mono- or polycyclic ring which has one or more heteroatoms selected from O, N or S, preferably 1 or 2 heteroatoms which are the same or different, but does not have aromatic rings, including pyrolidine, imidazoline, imidazolidine, pyrozoline, pyrozolidine, piperidine, morpholine, piperazine and etc, preferably morpholine, piperazine and etc. The heterocyclic radical can have one or more substituent groups such as halogen, $C_{1-6}$ alkyl, $C_{1-6}$ halogenoalkyl, $C_{1-6}$ alkoxy, amino group etc.

In a preferred embodiment, the present invention relates to a quinoline derivative of formula 1 or its pharmaceutically acceptable salts:

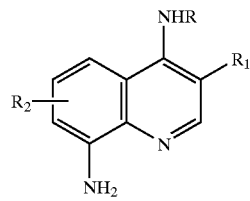

Formula 1 wherein

R₂ is H; halogen; $C_{1-6}$ alkyl; $C_{1-6}$ alkoxy; $C_{1-6}$ alkoxyalkyl; or $C_{3-6}$ cycloalkyl;

R₁ is

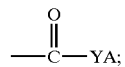

—CN; or

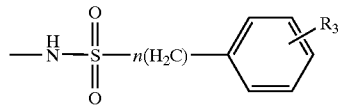

[wherein Y is O; or N;

A is H; $C_{3-6}$ alkenyl; $C_{3-6}$ cycloalkyl; $C_{6-14}$ aryl unsubstituted or substituted by halogen, $C_{1-6}$ alkyl or $C_{1-6}$ alkoxy; $C_{1-6}$ alkoxyalkyl; or $C_{1-6}$ alkyl unsubstituted or substituted by $C_{6-14}$ aryl or 5–15 membered heteroaryl (wherein the aryl group can be unsubstituted or substituted by halogen, $C_{1-6}$ alkyl, $C_{1-6}$ halogenoalkyl, $C_{1-6}$ alkoxy or amino group);

$R_3$ is H; halogen; unsubstituted or substituted amino; $C_{1-6}$ alkyl; $C_{1-6}$ alkoxy; $C_{1-6}$ alkoxyalkyl; or $C_{3-6}$ cycloalkyl;

n is 0, 1, 2 or 3];

R is H; $C_{6-14}$ aryl substituted by $C_{1-6}$ alkyl; 5–15 membered heterocyclic group substituted by $C_{1-6}$ alkyl; or —$(CH_2)_n$—$CHR_4R_5$ (wherein n is 0, 1, 2, 3 or 4;

$R_4$ is H; $C_{1-6}$ alkyl; $C_{1-6}$ alkoxy; $C_{6-14}$ aryl unsubstituted or substituted by halogen, $C_{1-6}$ alkyl, $C_{1-6}$ halogenoalkyl, $C_{1-6}$ alkoxy or amino; 5–15 membered heteroaryl; $C_{3-6}$ cycloalkyl; 5–15 membererd heterocyclic group; or $C_{6-14}$ aryl fused to 5–15 membered heterocyclic group;

$R_5$ is H; $C_{1-6}$ alkyl; $C_{1-6}$ alkoxy; or $C_{1-6}$ alkoxyalkyl).

In a more preferred embodiment, the present invention relates to a quinoline derivative of formula 1 or its pharmaceutically acceptable salts:

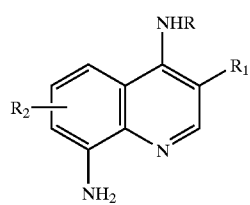

Formula 1 wherein
$R_2$ is H;
$R_1$ is

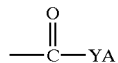

(wherein Y is O;
A is H; $C_{3-6}$ alkenyl; or $C_{1-6}$ alkyl);
R is H; or —$(CH_2)_n$—$CHR_4R_5$
(wherein n is 0, 1, 2 or 3;
$R_4$ is H; $C_{1-6}$ alkyl; $C_{1-6}$ alkoxy; $C_{6-14}$ aryl unsubstituted or substituted by halogen, $C_{1-6}$ alkyl, $C_{1-6}$ halogenoalkyl, $C_{1-6}$ alkoxy or amino; 5–15 membered heteroaryl; $C_{3-6}$ cycloalkyl; 5–15 membered heterocyclic group; or $C_{6-14}$ aryl fused to 5–15 membered heterocyclic group;

$R_5$ is H; $C_{1-6}$ alkyl; or $C_{1-6}$ alkoxyalkyl).

In an alternative more preferred embodiment, the present invention relates to a quinoline derivative of formula 1 or its pharmaceutically acceptable salts:

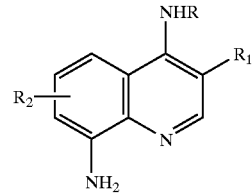

Formula 1 wherein
$R_2$ is H;
$R_1$ is

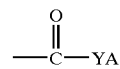

(wherein Y is O; A is ethyl; or propenyl);
R is H; or —$(CH_2)_n$—$CHR_4R_5$ (wherein n is 1, 2, 3 or 4; $R_4$ is methyl, ethyl, propyl, isopropyl, butyl or isobutyl; methoxy or ethoxy; phenyl or napthyl unsubstitued or substituted by chlorine, fluorine, methyl, methoxy, trifluoromethyl or amino; pyridyl; hexyl; morpholyl; thiopenyl; or benzo-dioxol; $R_5$ is H; methyl, ethyl, propyl, isopropyl, butyl or isobutyl; or methoxymethyl).

Preferred compounds of this invention include
8-amino-4-benzylamino-quinoline-3-carboxylic acid ethyl ester,
8-amino-4-cyclohexylamino-quinoline-3-carboxylic acid ethyl ester,
8-amino-4-[(naphthalene-1-ylmethyl)-amino]-quinoline-3-carboxylic acid ethyl ester,
8-amino-4-[(pyridine-2-ylmethyl)-amino]-quinoline-3-carboxylic acid ethyl ester,
8-amino-4-[(thiopen-2-ylmethyl)-amino]-quinoline-3-carboxylic acid ethyl ester,
8-amino-4-(3-morpholine-4-yl-propylamino)-quinoline-3-carboxylic acid ethyl ester,
8-amino-4-[(benzo[1,3]-dioxol-5-ylmethyl)-amino]-quinoline-3-carboxylic acid ethyl ester,
8-amino-4-(3-trifluoromethyl-benzylamino)-quinoline-3-carboxylic acid ethyl ester,
8-amino-4-(1-methoxymethyl-propylamino)-quinoline-3-carboxylic acid ethyl ester,
8-amino-4-butylamino-quinoline-3-carboxylic acid ethyl ester,
8-amino-4-isobutylamino-quinoline-3-carboxylic acid ethyl ester,
8-amino-4-isopropylamino-quinoline-3-carboxylic acid ethyl ester,
8-amino-4-(2-fluoro-benzylamino)-quinoline-3-carboxylic acid ethyl ester,
8-amino-4-(3-fluoro-benzylamino)-quinoline-3-carboxylic acid ethyl ester,
8-amino-4-(3-isopropoxy-propylamino)-quinoline-3-carboxylic acid ethyl ester,
8-amino-4-(2-methoxy-benzylamino)-quinoline-3-carboxylic acid ethyl ester,
8-amino-4-(4-methoxy-benzylamino)-quinoline-3-carboxylic acid ethyl ester,
8-amino-4-(3-methoxy-benzylamino)-quinoline-3-carboxylic acid ethyl ester, 8-amino-4-(2-methoxy-ethylamino)-quinoline-3-carboxylic acid ethyl ester,
8-amino-4-(4-methyl-benzylamino)-quinoline-3-carboxylic acid ethyl ester,
8-amino-4-phenethylamino-quinoline-3-carboxylic acid ethyl ester,
8-amino-4-(3-phenyl-propylamino)-quinoline-3-carboxylic acid ethyl ester,
8-amino-4-(4-phenyl-butylamino)-quinoline-3-carboxylic acid ethyl ester,
8-amino-4-(2-chlorobenzylamino)-quinoline-3-carboxylic acid ethyl ester,
8-amino-4-(4-chloro-benzylamino)-quinoline-3-carboxylic acid ethyl ester,
8-amino-4-propylamino-quinoline-3-carboxylic acid ethyl ester,
8-amino-4-[2-(2-aminophenyl)-ethylamino]-quinoline-3-carboxylic acid ethyl ester,
8-amino-4-(2-amino-benzylamino)-quinoline-3-carboxylic acid ethyl ester,
8-amino-4-(3-morpholine-4-yl-propylamino)-quinoline-3-carboxylic acid propenyl ester,
8-amino-4-(3-morpholine-4-yl-propylamino)-quinoline-3-carboxylic acid propyl ester,|
8-amino-4-[(pyridine-2-ylmethyl)-amino]-quinoline-3-carboxylic acid propyl ester, or their pharmaceutically acceptable salts.

The most preferred compounds of this invention include 8-amino-4-[(pyridine-2-ylmethyl)-amino]-quinoline-3-carboxylic acid ethyl ester, 8-amino-4-(3-morpholine-4-yl-propylamino)-quinoline-3-carboxylic acid ethyl ester, 8-amino-4-(3-isopropoxy-propylamino)-quinoline-3-carboxylic acid ethyl ester, 8-amino-4-(2-methoxy-ethylamino)-quinoline-3-carboxylic acid ethyl ester, or their pharmaceutically acceptable salts.

Quinoline derivatives of formula 1 of this invention can exist as pharmaceutically acceptable salts. The pharmaceutically acceptable salts of the compounds of this invention include ones derived from inorganic and organic acids and bases. The examples of suitable acids include chloric acid, bromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, citric acid, methanesulfonic acid, formic acid, benzoic acid, malonic acid, naphathalene-2-sulphonic acid, benzene sulfonic acid and etc. The salts derived from suitable bases include alkaline metal, for example, sodium, alkaline earth metal, for example magnesium, ammonium and etc.

The present invention relates to a method for preparing quinoline derivatives of formula 1 or their pharmaceutically acceptable salts.

In an embodiment, the present invention relates to a method for preparing the compound of formula 1a or its pharmaceutically acceptable salts, which is characterized by comprising the steps of:

1) reacting the compound of formula 2 with the compound of formula 3 without solvent at 100 to 150° C. with heating or with organic solvent (e.g., toluene, chlorobenzene, xylene and etc) at its boiling point to obtain the compound of formula 4;

2) cyclizing the compound of formula 4 in organic solvent (e.g., phenylether, diphenylether and etc.) at 200° C. to the boiling point of the solvent with heating to obtain the compound of formula 5;

3) reacting the compound of formula 5 with phosphorous oxychloride, phosphorous trichloride or phosphorous pentachloride to obtain the compound of formula 6 wherein X is halogen, or reacting the compound of formula 5 with sulphonylchloride or phosphorylchloride in organic solvent (e.g., dichlorormethane, chloroform, 1,2-dichlrorethane and etc.) with the addition of base (e.g., triethylamine, diisopropylethylamine, dimethylaniline, pyridine, quinoline and etc) at −10° C. to ambient temperature to obtain the compound of formula 6 wherein X is sulphonate or phosphonate;

4) reacting the compound of formula 6 with the amine of formula 7 in organic solvent (e. g., dichlorormethane, chloroform, tetrahydrofuran, dioxane, anisole, acetonitrile, propionitrile, dimethylformamide, dimethylsulfoxide and etc.) at ambient temperature to the boiling poing of the solvent to obtain the compound of formula 8;

5) hydrolyzing the compound of formula 8 with base (e. g., lithium hydroxide, sodium hydroxide, potassium hydroxide, sodium bicarbonate and etc.) in the solvent mixture of organic solvent (e. g., methanol, dioxane, anisole, acetonitrile, propionitrile, dimethylformamide, dimethylsulfoxide and etc.) and water to obtain the compound of formula 9;

6) reacting the compound of formula 9 with thionylchloride, sulphonylchloride or phosphorylchloride in organic solvent (e.g., dichloromethane, chloroform, 1,2-dichlrorethane and etc.) with the addition of base (e.g., triethylamine, diisopropylethylamine, dimethylaniline, pyridine, quinoline and etc.) at −10° C. to ambient temperature to obtain the compound of formula 10;

7) reacting the compound of formula 10 with the compound of formula 11 in organic solvent (e.g., dichloromethane, chloroform, tetrahydrofuran, dioxane, anisole, acetonitrile, propionitrile, dimethyformamide, dimethylsulfoxide and etc.) at ambient temperature to the boiling point of the solvent to obtain the compound of formula 12; and 8) reducing the compound of formula 12 with a metal catalyst (e.g., palladium/charcoal, platinum oxide etc.) and hydrogen gas in organic solvent (e.g., ethylacetate, methanol, ethanol, tetrahydrofuran, dioxane, anisole, acetonitrile, propionitrile, dimethylformamide, dimethylsulfoxide and etc.) at ambient temperature to obtain the compound of formula 1a.

The preparation method described in the above is shown in the following reaction scheme 1:

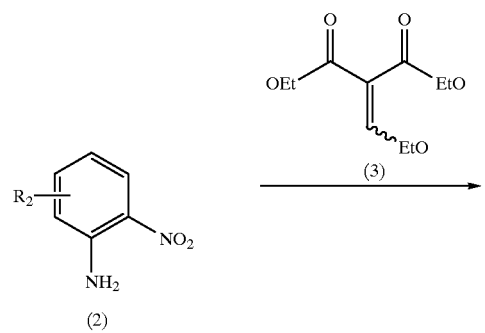

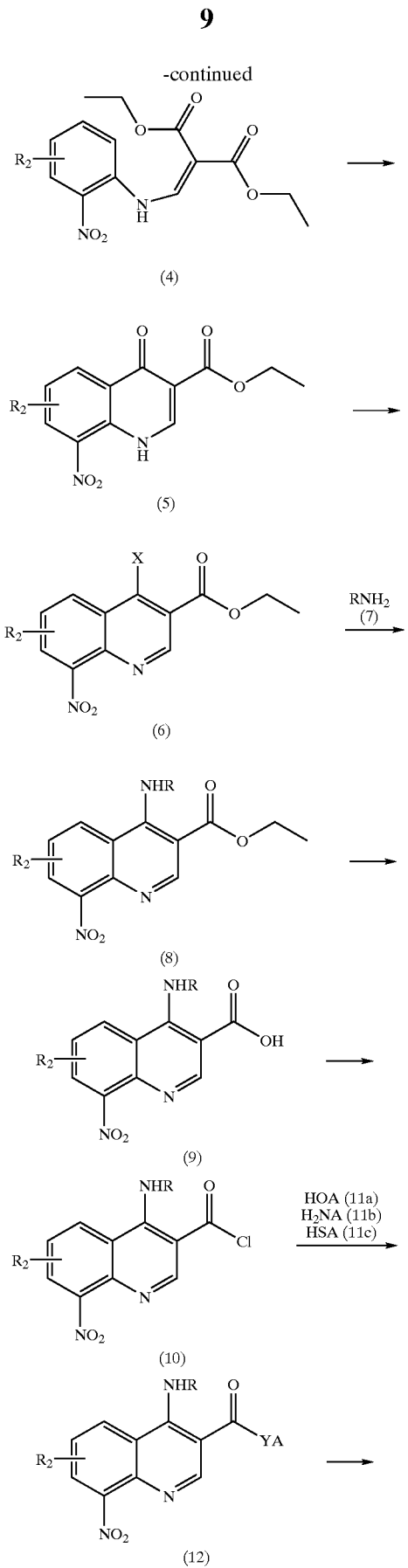

(4)

(5)

(6)

(8)

(9)

(10)

HOA (11a)
H₂NA (11b)
HSA (11c)

(12)

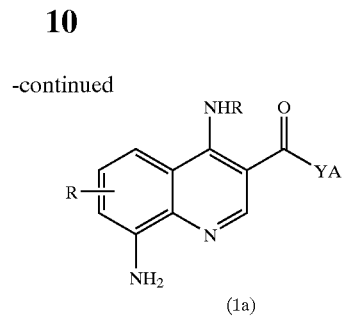

(1a)

wherein R, $R_1$, $R_2$ and A are defined as in the above and X is halogen, or sulphonate or phosphonate.

In the reaction step 4, the amine compound can be used in the amount of one equivalent or more. To help the reaction proceed more efficiently, base can be added. The base used includes inorganic base such as sodium carbonate, potassium carbonate, sodium bicarbonate and etc. and organic base such as triethylamine, diisopropylethylamine, dimethyaniline, pyridine, quinoline and etc. When base is not added, the amine compound is preferably used in an amount of 2 equivalents or more.

The ratio of organic solvent to water in the step 5 is preferably 1:1.

Amine, alcohole or thiol compound in the step 7 is used in an amount of one equivalent or more. To help the reaction proceed more efficiently, base can be added. The base used includes organic base such as triethylamine, diisopropylethylamine, dimethylaniline, pyridine, quinoline and etc. When base is not added, the amine compound can be preferably used in an amount of 2 equivalents or more.

In an alternative embodiment, the present invention relates to a method for preparing the compound of formula 1b or its pharmaceutically acceptable salt, which is characterized by comprising the steps of:

1) reacting the compound of formula 2 with the compound of formula 3 without solvent at 100 to 150° C. with heating or with organic solvent (e.g., toluene, chlorobenzene, xylene and etc) at its boiling point to obtain the compound of formula 4;

2) cyclizing the compound of formula 4 in organic solvent (e.g., phenylether, diphenylether and etc.) at 200° C. to the boiling point of the solvent with heating to obtain the compound of formula 5;

3) reacting the compound of formula 5 with phosphorous oxychloride, phosphorous trichloride, or phosphorous pentachloride to obtain the compound of formula 6 wherein X is halogen, or reacting the compound of formula 5 with sulphonylchloride or phosphorylchloride in organic solvent (e.g., dichlorormethane, chloroform, 1,2-dichlroroethane and etc.) with the addition of base (e.g., triethylamine, diisopropylethylamine, dimethylaniline, pyridine, quinoline and etc) at −10° C. to ambient temperature to obtain the compound of formula 6 wherein X is sulphonate or phosphonate;

4) reacting the compound of formula 6 with the amine of formula 7 in organic solvent (e. g., dichlorormethane, chloroform, tetrahydrofuran, dioxane, anisole, acetonitrile, propionitrile, dimethylformamide, dimethylsulfoxide and etc.) at ambient temperature to the boiling poing of the solvent to obtain the compound of formula 8;

5) hydrolyzing the compound of formula 8 with base (e. g., lithium hydroxide, sodium hydroxide, potassium hydroxide, sodium bicarbonate and etc.) in the solvent mixture of organic solvent (e. g., methanol, dioxane, anisole, acetonitrile, propionitrile, dimethylformamide, dimethylsulfoxide and etc.) and water to obtain the compound of formula 9;

6) reacting the compound of formula 9 for Curtius rearrangement with sodium azide or diphenylphosphorylazide and amine in organic solvent (e.g., tertiary alcohol, benzene, toluene, dichloromethane, chloroform, tetrahydrofuran, dioxane, anisole, acetonitirile, propionitrile, dimethylformamide, dimethylsulfoxide and etc.) at the boiling point of the solvent to obtain the compound of formula 13;

7) reacting the compound of formula 13 with the substituted sulphonylchloride compound of formula 14 in organic solvent (e.g., dichloromethane, chloroform, dihydrofuran, anisole, acetonitrile, propionitrile, dimethylformamide, dimethylsulfoxide and etc.) at ambient temperature to the boiling point of the solvent to obtain the compound of formula 15;

8) reducing the compound of formula 15 with a metal catalyst (e.g., palladium/charcoal, platinum oxide etc.) and hydrogen gas in organic solvent (e.g., ethylacetate, methanol, ethanol, tetrahydrofuran, dioxane, anisole, acetonitrile, propionitrile, dimethylformamide, dimethylsulfoxide and etc.) at ambient temperature to obtain the compound of formula 1b.

The preparation method described in the above is shown in the following reaction scheme 2:

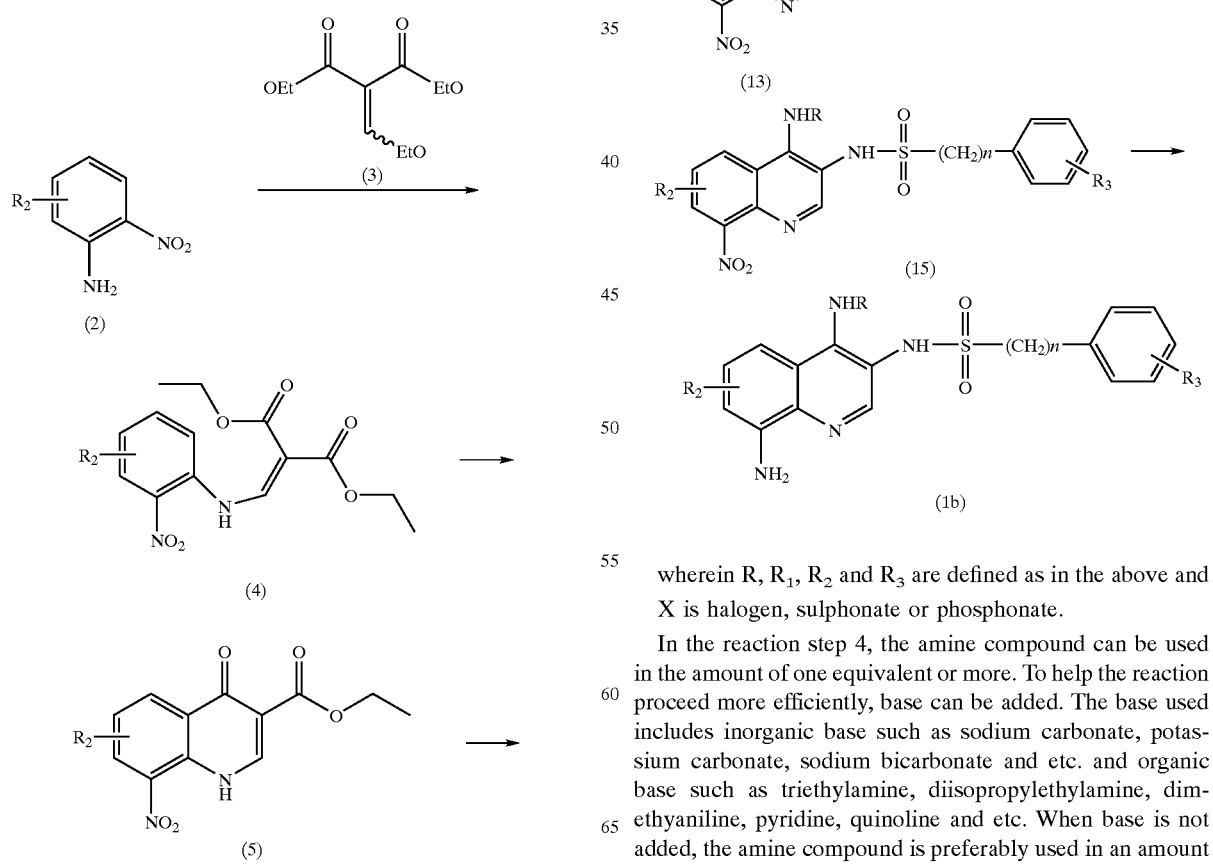

wherein R, $R_1$, $R_2$ and $R_3$ are defined as in the above and X is halogen, sulphonate or phosphonate.

In the reaction step 4, the amine compound can be used in the amount of one equivalent or more. To help the reaction proceed more efficiently, base can be added. The base used includes inorganic base such as sodium carbonate, potassium carbonate, sodium bicarbonate and etc. and organic base such as triethylamine, diisopropylethylamine, dimethyaniline, pyridine, quinoline and etc. When base is not added, the amine compound is preferably used in an amount of 2 equivalents or more.

The ratio of organic solvent to water in the step 5 is preferably 1:1.

To progress effectively the reaction in the step 6 base can be added. The base used includes triethylamine, diisopropylethylamine, dimethylaniline, pyridine, quinoline and etc.

The compound of formula 14 can be used in an amount of one equivalent or more. To help the reaction proceed more efficiently, base can be added. The base used includes organic base such as triethylamine, diisopropylethylamine, dimethylaniline, pyridine, quinoline and etc.

In an alternative embodiment, the present invention relates to a method for preparing the compound of formula 1c or its pharmaceutically acceptable salt which is characterized by comprising the steps of:

1) reacting the compound of formula 16 with the compound of formula 17 without solvent at 100 to 150° C. with heating or with organic solvent (e.g., toluene, chlorobenzene, xylene and etc) at its boiling point to obtain the compound of formula 18;

2) cyclizing the compound of formula 18 in organic solvent (e.g., phenylether, diphenylether and etc.) at 200° C. to the boiling point of the solvent with heating to obtain the compound of formula 19;

3) reacting the compound of formula 19 with phosphorous oxychloride, phosphorous trichloride or phosphorous pentachloride to obtain the compound of formula 20 wherein X is halogen, or reacting the compound of formula 19 with sulphonylchloride or phosphorylchloride in organic solvent (e.g., dichlorormethane, chloroform, 1,2-dichlroroethane and etc.) with the addition of base (e.g., triethylamine, diisopropylethylamine, dimethylaniline, pyridine, quinoline and etc) at −10° C. to ambient temperature to obtain the compound of formula 20 wherein X is sulphonate or phosphonate;

4) reacting the compound of formula 20 with the amine of formula 7 in organic solvent (e. g., dichlorormethane, chloroform, tetrahydrofuran, dioxane, anisole, acetonitrile, propionylnitrile, dimethylformamide, dimethylsulfoxide and etc.) at ambient temperature to the boiling poing of the solvent to obtain the compound of formula 21;

5) reducing the compound of formula 21 with a metal catalyst (e.g., palladium/charcoal, platinum oxide etc.) and hydrogen gas in organic solvent (e.g., ethylacetate, methanol, ethanol, tetrahydrofuran, dioxane, anisole, acetonitrile, propionitrile, dimethylformamide, dimethylsulfoxide and etc.) at ambient temperature to obtain the compound of formula 1c.

The preparation method described in the above is shown in the following reaction scheme 3:

Reaction scheme 3

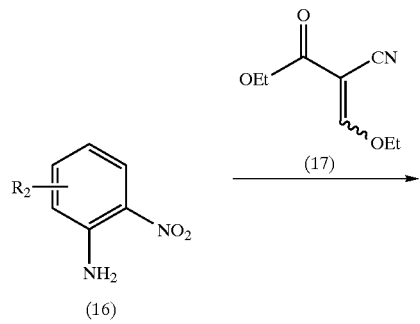

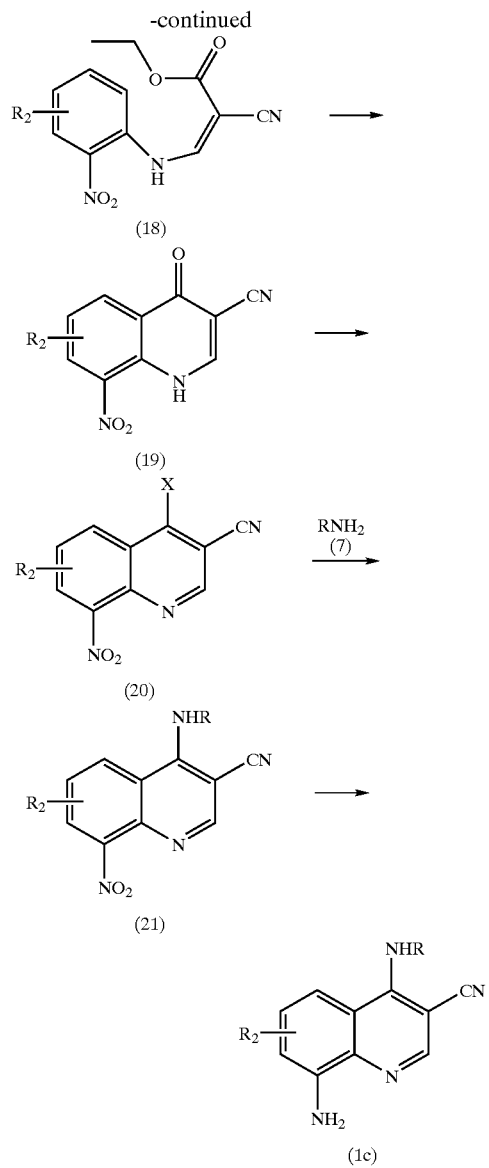

wherein R and $R_2$ are defined in the above and
X is halogen, sulphonate or phosphonate.

In the reaction step 3, the amine compound can be used in the amount of one equivalent or more. To help the reaction proceed more efficiently, base can be added. The base used includes inorganic base such as sodium carbonate, potassium carbonate, sodium bicarbonate and etc. and organic base such as triethylamine, diisopropylethylamine, dimethylaniline, pyridine, quinoline and etc. When base is not added, the amine compound is preferably used in an amount of 2 equivalents or more.

The compound of formula 1 of this invention can be used as a drug for treating Alzheimer's disease, Huntington's disease, Parkinson's disease, ALS, AIDS, stroke/ischemia, traumatic brain injury, spinal cord injury, osteoarthritis and etc. by inhibiting caspase-3.

The compound of this invention can be provided in the form of a pharmaceutical composition which comprises the compound of the invention alone or with pharmaceutically acceptable excipients. Pharmaceutically acceptable excipients which may be adjuvants or other vehicles include, but are not limited to, ion exchange resin, alumina, aluminium stearate, lecithin, serum protein (e.g., human serum albumin), buffer substance (e.g., various phosphate, glycine, sorbic acid, potassium sorbate, partial glyceride mixture of saturated vegetable fatty acid), water, salt or electrolyte (e.g., protamine sulfate, disodium hydrogen phosphate, potassium hydrogen phosphate, sodium chloride and zinc salt), colloidal silica, magnesium trisililcate, olyvinylpyrolidone, cellulose material, polyethylene glycol, sodium carboxymethylcellulose, polyarylate, wax, polyethylene-polyoxypropylene-block copolymer, wool fat and etc.

The pharmaceutical composition of this invention can be administered orally, parenterally, by inhalation spray, topically, rectally, bucally or vaginally or via an implanted reservoir when administered to a mammal (e.g., human). The parenteral administration can be accomplished by subcutaneous, intravenous, intramuscular, intra-articular, intrasynovial, intrasternal, intrathecal, intrahepatic, intralesional and intracranial injection or infusion techniques.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example a solution in 1,3-butanediol. Among the acceptable vehicles and solvents that may be employed mannitol, water, Ringer's solution and isotonic sodium chloride solution are included. In addition, sterile, fixed oils are conventionally employed as a solvent or suspending medium. For this prupose, any bland fixed oil may be employed including synthetic mono- or di-glycerides. Fatty acid, such as oleic acid and its glyceride derivatives are useful in the preparation of injectables, as are natural pharmaceutically acceptable oils, such as olive oil or castor oil, especially in their polyoxyethylated forms. These oil solutions or suspension may also contain a long-chain alcohol diluent or dispersant.

The pharmaceutical compositions of this invention may be orally administered in any orally acceptable dosage form including, but are not limited to, capsules, tablets, aqueous suspensions or solutions. In the case of tablets for oral use, carriers that are commonly used include lactose and corn starch. Lubrication agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical composition of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical composition of this invention may also be administered topically, especially when the target of treatment includes areas or organs readily accessible by topical application. For topical applications, the pharmaceutical composition may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

The pharmaceutical composition of this invention may be also formulated in a suitable lotion or cream containg the active component suspended or dissolved in one or more carriers. Carriers suitable for the formulation include, but are not limited to, mineral oil, sorbitan monostearate, polysolvate 60, cetyl ester wax, ceteary alcohol, 2-octyldodecanol, benzyl alcohol and water. Alternatively, the pharmaceutical composition of this invention may be formulated to be administrated in a rectal suppository or in a sutable enema formulation. Also, topically-transdermal patches and ophthalmic drops may be used.

The pharmaceutical composition of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, or other conventional solubilizing or dispersing agents.

It should also be understood that the amount of the active ingredients will depend upon a variety of factors, including the subject being treated, the severity of the particular disease, the mode of administration, sex, the judgment of the treating physician and etc. and can be easily determined by the person skilled in the art. Typically, it can be administered in an amount of 0.001 to 100 mg/kg/day, preferably 0.001 to 10 mg/kg/day.

In order that this invention be more fully understood, the following preparative and testing examples are set forth. These examples are for the purpose of illustration only and are not to be construed as limiting the scope of the invention in any way.

PREPARATION EXAMPLES

Example 1

Synthesis of
2-[(2-Nitro-phenylamino)-methylene]-malonic acid diethyl ester (Compound of Formula 4)

To a solution of 2-nitroaniline (20 g, 144.8 mmol) dissolved in 400 ml of dry-ethanol in a 500 ml round bottom flask was added dimethylethoxymethylene malonate (34 g, 159.3 mmol). The solution was heated and refluxed for 6 hrs at 120° C. with stirring. The reaction was monitered by TLC (n-hexane/ethyl acetate=3/1). After completing the reaction and cooling to room temperature, the resulting precipate was collected by filtration, and the residue was washed three times with 100 ml of n-hexane to give 2-[(2-Nitro-phenylamino)-methylene]-malonic acid diethyl ester (31 g, 100.6 mmol, yield 69%).

$^1$H NMR (300 MHz, CDCl$_3$): δ=8.55 (d, 1H, —NH CHC(CO$_2$CH$_2$CH$_3$)$_2$, J=13.00 Hz), 8.28 (dd, 1H, aromatic H, J=1.25, 1.19 Hz), 7.68 (t, 1H, aromatic H, J=4.06 Hz), 7.52 (d, 1H, aromatic H, J=8.34 Hz), 7.23 (m, 1H, aromatic H), 4.42 (q, 2H, —NHCHC(CO$_2$CH$_2$CH$_3$)$_2$), 4.30 (q, 2H, —NHCHC(CO$_2$CH$_2$CH$_3$)$_2$), 3.39 (m, 6H, —NHCHC (CO$_2$CH$_2$CH$_3$)$_2$)

Example 2

Synthesis of 8-Nitro-4-oxo-1,4-dihydro-quinoline-3-carboxylic acid ethyl ester (Compound of Formula 5)

A solution of 2-[(2-Nitro-phenylamino)-methylene]-malonic acid diethyl ester (10 g, 32.44 mmol) dissolved in 20 ml of diphenyl ether in a 250 ml round bottom flask was heated and refluxed for 5 hrs at 280° C. with stirring. The reaction was monitered by TLC (n-hexane/ethyl acetate=3/1). After completing the reaction and cooling to room temperature, 200 ml of diethylether was added to the mixture and the resulting precipitate was collected by filtration, and the residue was washed with 200 ml of diethyl ether to give 8-Nitro-4-oxo-1,4-dihydro-quinoline-3-carboxylic acid ethyl ester (6.5 g, 19.08 mmol, yield 59%).

$^1$H NMR (300 MHz, CDCl$_3$): δ=11.40 (s, 1H, —NHCH—), 8.88 (d, 1H, —NHCH—, J=7.17 Hz), 8.69 (d, 2H, aromatic H, J=6.84 Hz), 7.56 (t, 1H, aromatic H, J=4.06 Hz), 4.42 (q, 2H, —CH$_2$CH$_3$), 3.39 (t, 3H, —CH$_2$CH$_3$, J=7.08 Hz)

Example 3

Synthesis of 8-nitro-4-chloro-quinoline-3-carboxylic acid ethyl ester (Compound of Formula 6)

To a solution of 8-Nitro-4-oxo-1,4-dihydro-quinoline-3-carboxylic acid ethyl ester (10 g, 38.14 mmol) in 100 ml of thionyl chloride in a 250 ml round bottom flask was added a catalytic amount of 200 ul of dimethyl acetamide. The mixture was heated and refluxed for 2 hrs with stirring. The reaction was monitered by TLC (n-hexanelethyl acetate=3/1). After completing and cooling to room temperature, thiony chloride was removed under vacuum and 100 ml of water was added. The residue was extracted three times with 100 ml of ethyl acetate each time and the organic layer was dried over magnesium sulfate and filtrated. The residue was purified by column chromatography (hexan/ethyl acetate=3/1) to give 8-nitro-4-chloro-quinoline-3-carboxylic acid ethyl ester (9.5 g, 33.85 mmol, 89%)

$^1$H NMR (300 MHz, CDCl$_3$) δ=9.35 (s, 1H, —N=CH—), 8.67 (d, 1H, aromatic H, J=9.38 Hz), 8.17 (t, 1H, aromatic H, J=3.72 Hz), 7.82 (t, 1H, aromatic H, J=8.04 Hz), 4.54 (q, 2H, —CO$_2$CH$_2$CH$_3$), 1.48 (t, 3H, —CO$_2$CH$_2$CH$_3$, J=7.12 Hz)

Example 4

Synthesis of the Compound of Formula 8

To a solution of 8-nitro-4-chloro-quinolone-3-carboxylic acid ethyl ester (40 mg, 0.16 mmol) in 5 ml of acetonitrile in a 25 ml round bottom flask was added amine reagent. The mixture was heated and refluxed for 3 to 8 hrs with stirring. The reaction was monitered by TLC (n-hexane/ethyl acetate=3/1). After completing the reaction, 20 ml of water was added and the residue was extracted three times with 20 ml of ethyl acetate and the organic layer was dried over magnesium sulfate. The mixture was concentrated under vacuum. The residue was purified by column chromatography (hexane/ethyl acetate=3/1) to give a desired compound of formula 8.

Example 5

Synthesis of the Compound of Formula 9

To the solution of the compound of formula 8 in 4 ml of 50% methanol in 25 ml round bottom flask was added lithium hydroxide (80 mg, 4 equivalents). The mixture was stirred for 3 to 8 hrs at room temperature. The reaction was monitered by TLC (actenitrile/methnol=3/1). After completing the reaction, 20 ml of water was added and the mixture was extracted three times with 20 ml of ethyl acetate and the organic layer was dried over magnesium sulfate. The mixture was concentrated under vacuum. The residue was purified by column chromatography (acetonirile/methanol=3/1) to give a desired compound of formula 9.

Example 6

Synthesis of the Compound of Formula 10

To the compound of formula 9 in a 25 ml round bottom flask was added 5 ml of acetonitrile and the mixture was stirred. After cooling the flask to 0° C., thionyl chloride (0.21 ml, 3 mmol, 1.5 equivalents) was slowly added and stirred for 5 to 6 hrs. The reaction was monitered by TLC (n-hexane/ethyl acetate=3/1). After completing the reaction, thionyl chloride was removed under vacuum. The resulting residue was purified by column chromatography to give a desired compound of formula 10.

Example 7

Synthesis of the Compound of Formula 12

To the compound of formula 10 in a 25 ml round bottom flask was added 5 ml of acetonitrile and the mixture was stirred. To the mixture was added amine, alcohol or thiol. The mixture was heated and refluxed for 4–10 hrs with stirring. The reaction was monitered by TLC (n-hexane/ethyl acetate=3/1). After completing the reaction, 20 ml of water was added, the residue was extracted three times with 20 ml of ethyl acetate and the organic layer was dried over magnesium sulfate. The mixture was concentrated under vacuum. The residue was purified by column chromatography (hexane/ethyl acetate=3/1) to give a desired compound of formula 12.

Example 8

Synthesis of the Compound of Formula 13

To the compound of formula 9 in a 25 ml round bottom flask was added 7 ml of dry benzene with stirring. To the mixture was added amine with stirring and the flask was cooled to 0 to 5° C. After adding dropwise diphenylphosphoryl azide (0.11 ml, 0.5 mmol), the mixture was stirred for 3 hrs at room temperature and heated and refluxed for 5 hrs. The reaction was monitered by TLC (acetonitrile/methanol=3/1). After completing the reaction, to the mixture was added 14 ml of 50% sulfuric acid and the mixture was stirred for 24 hrs at room temperature. The reaction mixture was poured into ice-water, neutralized with concentrated NH4OH, and extracted three times with 20 ml of chloroform (20 ml×3). The combined extracts were washed with water, dried over magnesium sulfate and concentrated under reduced pressure. The residue was purified by column chromatography (acetonitrile/methanol=5/1) to give a desired compound of formula 13.

Example 9

Synthesis of the Compound of Formula 15

To the compound of formula 13 in a 25 ml round bottom flask was added 7 ml of dry tetrahydrofuran. After stirring the mixture and cooling the flask to 0 to 5° C., sulfonyl chloride and 0.1 ml of pyridine was added and stirred for 5 hrs at room temperature. The reaction was monitered by TLC (acetonitrile/methanol=3/1). After completing the reaction, the reaction solutione was extracted three times with 20 ml of chloroform (20 ml×3). The organic layer was dried over magnesium sulfate, and concentrated under reduced pressure. The residue was purified by column chromatography (acetonitrile/methanol=2/1) to give a desired compound of formula 15.

Example 10

Synthesis of the Compound of Formula 18

The mixture of 2-nitroaniline (60 g, 436 mmol) and ethyl 2-cyano-3-ethoxy acrylate (80 g, 480 mmol) was stirred for 12 hrs at 100° C. After completing the reaction, to the mixture was added diethylether and the resulting precipitate was collected by filtration to give the compound of formula 15 (94 g, 400 mmol, yield 83%).

$^1$H NMR (CDCl$_3$) 1.30 (t, 3H) 4.30–4.50 (m, 2H) 7.20–7.50 (m, 2H) 7.70–7.80 (m, 1H) 7.90–8.00 (d, 1H) 8.30–8.40 (d, 1H)

Example 11

Synthesis of 8-nitro-3-quinolone carbonitrile (Compound of Formula 19)

The mixture of diphenyl ether (250 g) and diphenyl ether (250 g) was stirred and heated to reflux. To that solution was dropwisely added the compound of formula 18 (15 g, 57 mmol) and the mixture was stirred for 4 hrs. After completing the reaction, to the mixture was added n-hexane, and the resulting precipitate was collected by filtration and washed with diethyl ether to obtain the compound of formula 19 (9 g, 42 mmol, yield 73%).

$^1$H NMR (DMSO-d$_6$) 7.60–7.80 (t, 1H) 8.50–8.80 (m, 3H) 12.50 (brs, 1H)

Example 12

Synthesis of 4-chloro-8-nitro-3-quinoline carbonitrile (Compound of Formula 20)

To the mixture of 8-nitro-3-quinoline carbonitrile (1 g, 4.9 mmol) and phosphorous oxychloride (7.5 g, 49 mmol) was dropwisely added a catalytic amount (5 drops) of dimethylformamide. The mixture was stirred and refluxed for 12 hrs. After completing the reaction, phosphorous oxychloride was removed under vacuum. The resulting mixture was neutralized with 20% NaOH solution, extracted with chloroform, concentrated under vacuum to remove chloroform and washed with ethyl acetate. The residue was purified by column chromatography to give 8-nitro-4-chloro-quinoline-3-carboxylic acid ethyl ester (0.5 g, 2 mmol, 45%)

$^1$H NMR (DMSO-d$_6$) 8.00–8.15 (t, 1H) 8.60–8.70 (m, 2H) 9.40 (s, 1H)

Example 13

Synthesis of the Compound of Formula 21

To a solution of 4-chloro-8-nitro-3-quinoline in 20 ml of acetonitrile was added amine. The mixture was stirred for 12 hrs. Acetonitrile was removed under vacuum. The resulting mixture was extracted with chloroform, washed with aqueous sodium bicarbonate solution, dried over magnesium sulfate, and concentrated under vacuum. The residue was purified by column chromatography to obtain a desired compound of formula 21.

Example 14

Synthesis of the Compound of Formula 1a

To the solution of the compound of formula 8 or formula 12 in 50 ml of dry tetrahydrofuran was added a catalytic amount of 10% palladium. The mixture was stirred for 3 hrs under hydrogen atmosphere. The resulting mixture was filtered with celite pad and the filtrate was concentrated under vacuum. The residue was purified by recrystallization (methylene chloride) to obtain a desired compound of formula 1a.

Example 15

Synthesis of the Compound of Formula 1b

To the solution of the compound of formula 15 in 20 ml of dry dimethylformamide was added a catalytic amount of platinum oxide (0.1 g, 0.43 mmol). The mixture was stirred for 18 hrs under hydrogen atmosphere. The resulting mixture was filtered with celite pad and the filtrate was concentrated under vacuum. The residue was purified by column chromatography to obtain a desired compound of formula 1b.

Example 16

Synthesis of the Compound of Formula 1c

To the solution of the compound of formula 21 in 10 ml of dry dimethyl formamide was added a catalytic amount of platinum oxide (0.1 g, 0.43 mmol). The mixture was stirred for 12 hrs under hydrogen atmosphere. The resulting mixture was filtered with celite pad and the filtrate was concentrated under vacuum. The residue was purified by column chromatography to obtain a desired compound of formula 1c.

Example 17

Synthesis of 8-Amino-4-benzylamino-quinoline-3-carboxylic acid ethyl ester

The compound prepared in Example 3 was reacted with benzylamine according to the method as described in Example 4 and the obtained compound was treated as described in Example 14 to prepare the title compound.

$^1$H NMR (300 MHz, CDCl$_3$): δ=9.32 (S, 1H, —NHCH$_2$—), 9.04 (s, 1H, —N═CH—), 7.55 (d, 1H, aromatic H, J=9.14 Hz), 7.32 (d, 2H, aromatic H, J=8.56 Hz), 7.16 (t, 1H, aromatic H, J=8.02 Hz), 6.94 (m, 3H, aromatic H), 4.97 (br, 2H, —NH$_2$), 4.92 (d, 2H, —NHCH$_2$—, J=5.54 Hz), 4.35 (q, 2H, —CO$_2$CH$_2$CH$_3$), 1.40 (t, 3H, —CO$_2$CH$_2$CH$_3$, J=7.12 Hz)

Example 18

Synthesis of 8-Amino-4-cyclohexylamino-quinoline-3-carboxylic acid ethyl ester

The compound prepared in Example 3 was reacted with cyclohexylamine according to the method as described in Example 4 and the obtained compound was treated as described in Example 14 to prepare the title compound (yield 88%).

$^1$H NMR (300 MHz, CDCl$_3$): δ=9.03 (s, 1H, —N=C$\underline{H}$—), 8.94 (S, 1H, —N$\underline{H}$CH$_2$—, J=8.56 Hz), 7.45 (d, 1H, aromatic H, J=8.47 Hz), 7.19 (t, 1H, aromatic H, J=8.01 Hz), 6.94 (d, 1H, aromatic H, J=7.46 Hz), 5.08 (br, 2H, —N$\underline{H_2}$), 4.37 (q, 2H, —CO$_2$C$\underline{H_2}$CH$_3$), 4.06 (q, 1H, cyclohexyl), 2.10 (d, 2H, cyclohexyl, J=10.93 Hz), 1.80 (d, 2H, cyclohexyl, J=8.13 Hz), 1.64 (t, 1H, cyclohexyl, J=4.88 Hz), 1.36 (m, 8H, —CO$_2$CH$_2$C$\underline{H_3}$, cyclohexyl)

Example 19

Synthesis of 8-Amino-4-[(naphthalen-1-ylmethyl)-amino]-quinoline-3-carboxylic acid ethyl ester The compound prepared in Example 3 was reacted with 1-naphthalenmethyl-amine according to the method as described in Example 4 and the obtained compound was treated as described in Example 14 to prepare the title compound (yield 80%).

$^1$H NMR (300 MHz, CDCl$_3$): δ=9.34 (S, 1H, —N$\underline{H}$CH$_2$—), 9.07 (s, 1H, —N=C$\underline{H}$—), 7.90 (m, 3H, aromatic H), 7.72 (d, 1H, aromatic H, J=6.73 Hz), 7.53 (m, 4H, aromatic H), 6.94 (d, 1H, aromatic H, J=7.21 Hz), 5.40 (d, 2H, —NHC$\underline{H_2}$—, J=5.23 Hz), 5.05 (br, 2H, —N$\underline{H_2}$), 4.28 (q, 2H, —CO$_2$C$\underline{H_2}$CH$_3$), 1.32 (t, 3H, —CO$_2$CH$_2$C$\underline{H_3}$, J=6.96 Hz)

Example 20

Synthesis of 8-Amino-4-[(pyridin-2-ylmethyl)-amino]-quinoline-3-carboxylic acid ethyl ester The compound prepared in Example 3 was reacted with (2-aminomethyl)pyridine according to the method as described in Example 4 and the obtained compound was treated as described in Example 14 to prepare the title compound (yield 85%).

$^1$H NMR (300 MHz, CDCl$_3$): δ=9.80 (S, 1H, —N$\underline{H}$CH$_2$—), 9.06 (s, 1H, —N=C$\underline{H}$—), 8.68 (d, 1H, aromatic H, J=4.37 Hz), 7.53 (d, 1H, aromatic H, J=8.50 Hz), 7.43 (d, 1H, aromatic H, J=7.77 Hz), 7.27 (t, 1H, aromatic H, J=2.20 Hz), 7.14 (t, 1H, aromatic H, J=8.04 Hz), 6.93 (d, 1H, aromatic H, J=7.41 Hz), 5.21 (d, 2H, —NHC$\underline{H_2}$—, J=5.70 Hz), 4.91 (br, 2H, —N$\underline{H_2}$), 4.42 (q, 2H, —CO$_2$C$\underline{H_2}$CH$_3$), 1.44 (t, 3H, —CO$_2$CH$_2$C$\underline{H_3}$, J=7.09 Hz)

Example 21

Synthesis of 8-Amino-4-[(thiophen-2-ylmethyl)-amino]-quinoline-3-carboxylic acid ethyl ester The compound prepared in Example 3 was reacted with thiophen-2-ylmethyl-amine according to the method as described in Example 4 and the obtained compound was treated as described in Example 14 to prepare the title compound (yield 89%).

$^1$H NMR (300 MHz, CDCl$_3$): δ=9.27 (S, 1H, —N$\underline{H}$CH$_2$—), 9.06 (s, 1H, —N=C$\underline{H}$—), 7.55 (d, 1H, aromatic H, J=8.58 Hz), 7.29 (dd, 1H, thiophene H, J=1.00 Hz, 1.28 Hz), 7.20 (t, 1H, aromatic H, J=7.86 Hz), 7.09 (d, 1H, thiophene H, J=2.66 Hz), 7.01 (m, 1H, thiophene H), 6.96 (d, 1H, aromatic H, J=8.06 Hz), 5.13 (d, 2H, —NHC$\underline{H_2}$—, J=5.62 Hz), 4.97 (br, 2H, —N$\underline{H_2}$), 4.37 (q, 2H, —CO$_2$C$\underline{H_2}$CH$_3$), 1.41 (t, 3H, —CO$_2$CH$_2$C$\underline{H_3}$, J=7.11 Hz)

Example 22

Synthesis of 8-Amino-4-(3-morpholin-4-yl-propylamino)-quinoline-3-carboxylic acid ethyl ester The compound prepared in Example 3 was reacted with 4-(3-aminopropyl)morpholine according to the method as described in Example 4 and the obtained compound was treated as described in Example 14 to prepare the title compound (yield 92%).

$^1$H NMR (300 MHz, CDCl$_3$): δ=9.12 (S, 1H, —N$\underline{H}$CH$_2$—), 9.00 (s, 1H, —N=C$\underline{H}$—), 7.56 (d, 1H, aromatic H, J=8.30 Hz), 7.18 (t, 1H, aromatic H, J=8.01 Hz), 6.94 (d, 1H, aromatic H, J=7.21 Hz), 4.95 (br, 2H, —N$\underline{H_2}$), 4.38 (q, 2H, —CO$_2$C$\underline{H_2}$CH$_3$), 3.85 (q, 2H, —NH C$\underline{H_2}$CH$_2$CH$_2$—), 3.70 (t, 4H, —NCH$_2$C$\underline{H_2}$O—, J=4.51 Hz), 2.46 (q, 4H, —N—C$\underline{H_2}$CH$_2$O—), 1.92 (t, 2H, —NHCH$_2$C$\underline{H_2}$CH$_2$—, J=6.89 Hz), 1.42 (t, 3H, —CO$_2$CH$_2$C$\underline{H_3}$, J=7.10 Hz)

Example 23

Synthesis of 8-Amino-4-[(benzo[1,3]dioxol-5-ylmethyl)-amino]-quinoline-3-carboxylic acid ethyl ester The compound prepared in Example 3 was reacted with piperonylamine according to the method as described in Example 4 and the obtained compound was treated as described in Example 14 to prepare the title compound (yield 91%).

$^1$H NMR (300 MHz, CDCl$_3$): δ=9.31 (S, 1H, —N$\underline{H}$CH$_2$—), 9.05 (s, 1H, —N=C$\underline{H}$—), 7.51 (d, 1H, aromatic H, J=8.53 Hz), 7.15 (t, 1H, aromatic H, J=8.03 Hz), 6.94 (d, 1H, aromatic H, J=7.49 Hz), 6.85 (m, 3H, aromatic H), 4.97 (br, 2H, —N$\underline{H_2}$), 4.88 (d, 2H, —NHC$\underline{H_2}$—, J=5.62 Hz), 4.37 (q, 2H, —CO$_2$C$\underline{H_2}$CH$_3$), 1.41 (t, 3H, —CO$_2$CH$_2$C$\underline{H_3}$, J=14.22 Hz)

Example 24

Synthesis of 8-Amino-4-(3-trifluoromethyl-benzylamino)-quinoline-3-carboxylic acid ethyl ester The compound prepared in Example 3 was reacted with 3-trifluoromethyl-benzylamine according to the method as described in Example 4 and the obtained compound was treated as described in Example 14 to prepare the title compound (yield 80%).

$^1$H NMR (300 MHz, CDCl$_3$): δ=9.35 (S, 1H, —N$\underline{H}$CH$_2$—), 9.08 (s, 1H, —N=C$\underline{H}$—), 7.59 (m, 4H, aromatic H), 7.38 (d, 1H, aromatic H, J=8.49 Hz), 7.14 (t, 1H, aromatic H, J=8.04 Hz), 6.94 (d, 1H, aromatic H, J=7.48 Hz), 5.02 (d, 2H, —NHC$\underline{H_2}$—, J=6.21 Hz), 4.38 (q, 2H, —CO$_2$C$\underline{H_2}$CH$_3$), 1.43 (t, 3H, —CO$_2$CH$_2$C$\underline{H_3}$, J=7.07 Hz)

Example 25

Synthesis of 8-Amino-4-(1-methoxymethyl-propylamino)-quinoline-3-carboxylic acid ethyl ester The compound prepared in Example 3 was reacted with 1-methoxy-2-aminobutane according to the method as described in Example 4 and the obtained compound was treated as described in Example 14 to prepare the title compound (yield 80%).

$^1$H NMR (300 MHz, CDCl$_3$): δ=9.04 (s, 1H, —N═C$\underline{H}$—), 8.91 (d, 1H, —N$\underline{H}$CH—, J=8.56 Hz), 7.50 (d, 1H, aromatic H, $\underline{J}$=8.62 Hz), 7.20 (t, 1H, aromatic H, J=8.01 Hz), 6.94 (d, 1H, aromatic H, J=7.47 Hz), 4.96 (br, 2H, —NH$_2$), 4.38 (q, 2H, —CO$_2$C$\underline{H_2}$CH$_3$), 4.15 (m, 1H, —C$\underline{H}$(CH$_2$CH$_3$)CH$_2$OCH$_3$), 3.52 (m, 2H, —CH(CH$_2$CH$_3$)C$\underline{H_2}$OCH$_3$), 3.37 (s, 3H, —CH(CH$_2$CH$_3$)CH$_2$OC$\underline{H_3}$), 1.75 (m, 2H, —CH(C$\underline{H_2}$CH$_3$)CH$_2$OCH$_3$), 1.44 (t, 3H, —CO$_2$CH$_2$C$\underline{H_3}$, J=7.11 Hz), 0.99 (t, 3H, —CH(CH$_2$C$\underline{H_3}$)CH$_2$OCH$_3$, J=7.43 Hz)

Example 26

Synthesis of 8-Amino-4-butylamino-quinoline-3-carboxylic acid ethyl ester

The compound prepared in Example 3 was reacted with butylamine according to the method as described in Example 4 and the obtained compound was treated as described in Example 14 to prepare the title compound (yield 78%).

$^1$H NMR (300 MHz, CDCl$_3$): δ=9.22 (S, 1H, —N$\underline{H}$CH$_2$—), 9.01 (s, 1H, —N═C$\underline{H}$—), 7.60 (d, 1H, aromatic H, J=8.58 Hz), 7.17 (t, 1H, aromatic H, J=8.05 Hz), 6.94 (d, 1H, aromatic H, J=7.50 Hz), 4.95 (br, 2H, —N$\underline{H_2}$), 4.38 (q, 2H, —CO$_2$C$\underline{H_2}$CH$_3$), 3.83 (q, 2H, —NHC$\underline{H_2}$CH$_2$CH$_2$CH$_3$), 1.76 (m, 2H, —NHCH$_2$C$\underline{H_2}$CH$_2$CH$_3$), 1.73 (m, 5H, —NHCH$_2$CH$_2$C$\underline{H_2}$CH$_3$, —CO$_2$CH$_2$C$\underline{H_3}$) 0.98 (t, 3H, —NHCH$_2$CH$_2$CH$_2$C$\underline{H_3}$, J=7.32 Hz)

Example 27

Synthesis of 8-Amino-4-isobutylamino-quinoline-3-carboxylic acid ethyl ester The compound prepared in Example 3 was reacted with isobutylamine according to the method as described in Example 4 and the obtained compound was treated as described in Example 14 to prepare the title compound (yield 82%).

$^1$H NMR (300 MHz, CDCl$_3$): δ=9.25 (S, 1H, —N$\underline{H}$CH$_2$—), 9.02 (s, 1H, —N═C$\underline{H}$—), 7.57 (d, 1H, aromatic H, J=8.57 Hz), 7.17 (t, 1H, aromatic H, J=8.02 Hz), 6.94 (d, 1H, aromatic H, J=7.49 Hz), 4.95 (br, 2H, —N$\underline{H_2}$), 4.39 (q, 2H, —CO$_2$C$\underline{H_2}$CH$_3$), 3.66 (t, 2H, —NHC$\underline{H_2}$CH(CH$_3$)$_2$, J=5.66 Hz), 1.99 (m, 1H, —NHCH$_2$C$\underline{H}$(CH$_3$)$_2$), 1.43 (t, 3H, —CO$_2$CH$_2$C$\underline{H_3}$, J=7.10 Hz) 0.98 (d, 6H, —NHCH$_2$CH(C$\underline{H_3}$)$_2$ J=6.67 Hz)

Example 28

Synthesis of 8-Amino-4-isopropylamino-quinoline-3-carboxylic acid ethyl ester The compound prepared in Example 3 was reacted with isopropylamine according to the method as described in Example 4 and the obtained compound was treated as described in Example 14 to prepare the title compound (yield 80%).

$^1$H NMR (300 MHz, CDCl$_3$): δ=9.03 (s, 1H, —N═C$\underline{H}$—), 8.85 (S, 1H, —N$\underline{H}$CH(CH$_3$)$_2$—), 7.48 (d, 1H, aromatic H, J=8.58 Hz), 7.20 (t, 1H, aromatic H, J=8.04 Hz), 6.94 (d, 1H, aromatic H, J=8.27 Hz), 4.96 (br, 2H, —N$\underline{H_2}$), 4.39 (m, 3H, —CO$_2$C$\underline{H_2}$CH$_3$, —N$\underline{H}$CH(CH$_3$)$_2$), 1.44 (t, 3H, —CO$_2$CH$_2$C$\underline{H_3}$, J=5.47 Hz) 1.38 (m, 6H, —NHCH(C$\underline{H_3}$)$_2$)

Example 29

Synthesis of 8-Amino-4-(2-fluoro-benzylamino)-quinoline-3-carboxylic acid ethyl ester The compound prepared in Example 3 was reacted with 2-fluoro-benzylamine according to the method as described in Example 4 and the obtained compound was treated as described in Example 14 to prepare the title compound (yield 92%).

$^1$H NMR (300 MHz, CDCl$_3$): δ=9.26 (S, 1H, —N$\underline{H}$CH$_2$—), 9.06 (s, 1H, —N═C$\underline{H}$—), 7.48 (m, 2H, aromatic H), 7.29 (m, 1H, aromatic H), 7.16 (m, 3H, aromatic H), 6.94 (d, 1H, aromatic H, J=8.03 Hz), 5.01 (d, 2H, —NHC$\underline{H_2}$—, J=6.07 Hz), 4.37 (q, 2H, —CO$_2$C$\underline{H_2}$CH$_3$), 1.42 (t, 3H, CO$_2$CH$_2$C$\underline{H_3}$, J=7.12 Hz)

Example 30

Synthesis of 8-Amino-4-(3-fluoro-benzylamino)-quinoline-3-carboxylic acid ethyl ester The compound prepared in Example 3 was reacted with 3-fluoro-benzylamine according to the method as described in Example 4 and the obtained compound was treated as described in Example 14 to prepare the title compound (yield 90%).

$^1$H NMR (300 MHz, CDCl$_3$): δ=9.26 (S, 1H, —N$\underline{H}$CH$_2$—), 9.06 (s, 1H, —N═C$\underline{H}$—), 7.40 (m, 2H, aromatic H), 7.15 (m, 3H, aromatic H), 7.02 (t, 1H, aromatic H, J=8.02 Hz), 6.93 (d, 1H, aromatic H, J=8.15 Hz), 4.96 (d, 2H, —NHC$\underline{H_2}$—, J=6.14 Hz), 4.39 (q, 2H, —CO$_2$C$\underline{H_2}$CH$_3$), 1.43 (t, 3H, —CO$_2$CH$_1$C$\underline{H_3}$, J=7.11 Hz)

Example 31

Synthesis of 8-Amino-4-(3-isopropoxy-propylamino)-quinoline-3-carboxylic acid ethyl ester The compound prepared in Example 3 was reacted with 3-isopropoxy-propylamine according to the method as described in Example 4 and the obtained compound was treated as described in Example 14 to prepare the title compound (yield 88%).

$^1$H NMR (300 MHz, CDCl$_3$): δ=9.18 (S, 1H, —N$\underline{H}$CH$_2$—), 9.00 (s, 1H, —N═C$\underline{H}$—), 7.58 (d, 1H, aromatic H, J=8.57 Hz), 7.17 (t, 1H, aromatic H, J=8.05 Hz), 6.93 (d, 1H, aromatic H, J=8.43 Hz), 4.95 (br, 2H, —N$\underline{H_2}$), 4.38 (q, 2H, —CO$_2$C$\underline{H_2}$CH$_3$), 3.91 (m, 2H, —NHC$\underline{H_2}$CH$_2$CH$_2$OCH(CH$_3$)$_2$), 3.55 (m, 3H, —NHCH$_2$CH$_2$C$\underline{H_2}$OC$\underline{H}$(CH$_3$)$_2$), 2.00 (m, 2H, —NHCH$_2$C$\underline{H_2}$CH$_2$OCH(CH$_3$)$_2$), 1.43 (t, 3H, —CO$_2$CH$_2$C$\underline{H_3}$, J=7.11 Hz), 1.13 (d, 6H, —NHCH$_2$CH$_2$CH$_2$OCH(C$\underline{H_3}$)$_2$, J=6.07 Hz)

Example 32

Synthesis of 8-Amino-4-(2-methoxy-benzylamino)-quinoline-3-carboxylic acid ethyl ester The compound prepared in Example 3 was reacted with 2-methoxy-benzylamine according to the method as described in Example 4 and the obtained compound was treated as described in Example 14 to prepare the title compound (yield 89%).
$^1$H NMR (300 MHz, CDCl$_3$): δ=9.28 (S, 1H, —NHCH$_2$—), 9.04 (s, 1H, —N=CH—), 7.51 (d, 1H, aromatic H, J=8.58 Hz), 7.42 (m, 1H, aromatic H), 7.31 (m, 1H, aromatic H), 7.14 (t, 1H, aromatic H, J=8.04 Hz), 6.92 (m, 3H, aromatic H), 4.94 (d, 2H, —NHCH$_2$—, J=5.92 Hz), 4.36 (q, 2H, —CO$_2$CH$_2$CH$_3$), 3.84 (s, 3H, —OCH$_3$), 1.40 (t, 3H, —CO$_2$CH$_2$CH$_3$, J=7.10 Hz)

Example 33

Synthesis of 8-Amino-4-(4-methoxy-benzylamino)-quinoline-3-carboxylic acid ethyl ester The compound prepared in Example 3 was reacted with 4-methoxy-benzylamine according to the method as described in Example 4 and the obtained compound was treated as described in Example 14 to prepare the title compound (yield 87%).
$^1$H NMR (300 MHz, CDCl$_3$): δ=9.32 (S, 1H, —NHCH$_2$—), 9.04 (s, 1H, —N=CH—), 7.55 (d, 1H, aromatic H, J=9.14 Hz), 7.32 (d, 2H, aromatic H, J=8.56 Hz), 7.16 (t, 1H, aromatic H, J=8.02 Hz), 6.94 (m, 3H, aromatic H), 4.97 (br, 2H, —NH$_2$), 4.92 (d, 2H, —NHCH$_2$—, J=5.54 Hz), 4.35 (q, 2H, —CO$_2$CH$_2$CH$_3$), 3.83 (s, 3H, —OCH$_3$), 1.40 (t, 3H, —CO$_2$CH$_2$CH$_3$, J=7.12 Hz)

Example 34

Synthesis of 8-Amino-4-(3-methoxy-benzylamino)-quinoline-3-carboxylic acid ethyl ester The compound prepared in Example 3 was reacted with 3-methoxy-benzylamine according to the method as described in Example 4 and the obtained compound was treated as described in Example 14 to prepare the title compound (yield 85%).
$^1$H NMR (300 MHz, CDCl$_3$): δ=9.32 (S, 1H, —NHCH$_2$—), 9.06 (s, 1H, —N=CH—), 7.50 (d, 1H, aromatic H, J=9.23 Hz), 7.30 (t, 1H, aromatic H, J=7.86 Hz), 7.12 (t, 1H, aromatic H, J=8.46 Hz), 6.93 (m, 4H, aromatic H), 4.96 (d, 2H, —NHCH$_2$—, J=5.91 Hz), 4.37 (q, 2H, —CO$_2$CH$_2$CH$_3$), 3.82 (s, 3H, —OCH$_3$), 1.42 (t, 3H, —CO$_2$CH$_2$CH$_3$, J=7.12 Hz)

Example 35

Synthesis of 8-Amino-4-(2-methoxy-ethylamino)-quinoline-3-carboxylic acid ethyl ester The compound prepared in Example 3 was reacted with 2-methoxy-ethylamine according to the method as described in Example 4 and the obtained compound was treated as described in Example 14 to prepare the title compound (yield 89%).
$^1$H NMR (300 MHz, CDCl$_3$): δ=9.25 (S, 1H, —NHCH$_2$—), 9.02 (s, 1H, —N=CH—), 7.53 (d, 1H, aromatic H, J=9.11 Hz), 7.18 (t, 1H, aromatic H, J=8.04 Hz), 6.93 (d, 1H, aromatic H, J=8.12 Hz), 4.96 (br, 2H, —NH$_2$), 4.40 (q, 2H, —CO$_2$CH$_2$CH$_3$), 3.98 (q, 2H, —NH CH$_2$CH$_2$OCH$_3$), 3.65 (t, 2H, —NHCH$_2$CH$_2$OCH$_3$, J=5.25 Hz), 3.46 (s, 3H, —NHCH$_2$CH$_2$OCH$_3$), 1.43 (t, 3H, —CO$_2$CH$_2$CH$_3$, J=7.01 Hz)

Example 36

Synthesis of 8-Amino-4-(1-phenyl-ethylamino)-quinoline-3-carboxylic acid ethyl ester The compound prepared in Example 3 was reacted with phenylethylamine according to the method as described in Example 4 and the obtained compound was treated as described in Example 14 to prepare the title. compund (yield 83%).
$^1$H NMR (300 MHz, CDCl$_3$): δ=9.36 (S, 1H, —NHCH$_2$—, J=8.08 Hz), 9.06 (s, 1H, —N=CH—), 7.44–7.28 (m, 6H, aromatic H), 7.05 (t, 1H, aromatic H, J=8.03 Hz), 6.88 (d, 1H, aromatic H, J=8.21 Hz), 5.37 (m, 1H, —NH(CH)CH$_3$—), 4.93 (br, 2H, —NH$_2$), 4.43 (q, 2H, —CO$_2$CH$_2$CH$_3$), 1.66 (d, 3H, —NH(CH)CH$_3$—, J=6.66 Hz), 1.46 (t, 3H, —CO$_2$CH$_2$CH$_3$, J=7.12 Hz)

Example 37

8-Amino-4-(4-methyl-benzylamino)-quinoline-3-carboxylic acid ethyl ester

The compound prepared in Example 3 was reacted reacted with 4-methyl-benzylamine according to the method as described in Example 4 and the obtained compound was treated as described in Example 14 to prepare the title compound (yield 83%).
$^1$H NMR (300 MHz, CDCl$_3$): δ=9.37 (S, 1H, —NHCH$_2$—), 9.06 (s, 1H, —N=CH—), 7.55 (d, 1H, aromatic H, J=8.51 Hz), 7.31–7.12 (m, 5H, aromatic H), 6.94 (d, 1H, aromatic H, J=8.36 Hz), 6.94 (d, 1H, aromatic H, J=8.36 Hz), 4.95 (d, 2H, —NHCH$_2$, J=5.66 Hz), 4.36 (q, 2H, —CO$_2$CH$_2$CH$_3$), 2.38 (s, 3H, —CH$_3$), 1.41 (t, 3H, —CO$_2$CH$_2$CH$_3$, J=7.12 Hz)

Example 38

Synthesis of 8-Amino-4-phenethylamino-quinoline-3-carboxylic acid ethyl ester

The compound prepared in Example 3 was reacted with phenethylamine according to the method as described in Example 4 and the obtained compound was treated as described in Example 14 to prepare the title compound (yield 88%).
$^1$H NMR (300 MHz, CDCl$_3$): δ=9.20 (S, 1H, —NHCH$_2$—), 9.02 (s, 1H, —N=CH—), 7.56 (d, 1H, aromatic H, J=8.45 Hz), 7.32 (m, 5H, aromatic H), 7.17 (t, 1H, aromatic H, J=8.01 Hz), 6.94 (d, 1H, aromatic H, J=7.45 Hz), 4.96 (br, 2H, —NH$_2$), 4.38 (q, 2H, —CO$_2$CH$_2$CH$_3$), 4.08 (m, 2H, —NHCH$_2$CH$_2$—), 3.06 (t, 2H, —NHCH$_2$CH$_2$—, J=7.45 Hz), 1.43 (t, 3H, —CO$_2$CH$_2$CH$_3$, J=7.11 Hz)

Example 39

Synthesis of 8-Amino-4-(3-phenyl-propylamino)-quinoline-3-carboxylic acid ethyl ester The compound prepared in Example 3 was reacted with 3-phenyl-propylamine according to the method as described in Example 4 and the obtained compound was treated as described in Example 14 to prepare the title compound (yield 88%).
$^1$H NMR (300 MHz, CDCl$_3$): δ=9.28 (S, 1H, —N<u>H</u>CH$_2$—), 9.04 (s, 1H, —N═C<u>H</u>—), 7.33–7.11 (m, 6H, aromatic H), 6.93 (d, 1H, aromatic H, J=7.48 Hz), 4.96 (br, 2H, —N<u>H</u>$_2$), 4.41 (q, 2H, —CO$_2$C<u>H</u>$_2$CH$_3$), 3.84 (m, 2H, —NHC<u>H</u>$_2$CH$_2$CH$_2$—, J=4.74 Hz), 2.79 (t, 2H, —NHCH$_2$CH$_2$C<u>H</u>$_2$—, J=7.61 Hz), 2.10 (t, 2H, —NHCH$_2$C<u>H</u>$_2$CH$_2$—, J=7.46 Hz), 1.45 (t, 3H, —CO$_2$CH$_2$C<u>H</u>$_3$, J=7.11 Hz)

Example 40

Synthesis of 8-Amino-4-(4-phenyl-butylamino)-quinoline-3-carboxylic acid ethyl ester The compound prepared in Example 3 was reacted with 4-phenyl1-1-butylamine according to the method as described in Example 4 and the obtained compound was treated as described in Example 14 to prepare the title compound (yield 88%).
$^1$H NMR (300 MHz, CDCl$_3$): δ=9.18 (S, 1H, —N<u>H</u>CH$_2$—), 9.03 (s, 1H, —N═C<u>H</u>—), 7.56 (d, 1H, aromatic H, J=8.57 Hz), 7.33–7.14 (m, 6H, aromatic H), 6.96 (d, 1H, aromatic H, J=7.44 Hz) 4.96 (br, 2H, —N<u>H</u>$_2$), 4.40 (q, 2H, —CO$_2$C<u>H</u>$_2$CH$_3$), 3.84 (d, 2H, —NHC<u>H</u>$_2$CH$_2$CH$_2$CH$_2$—, J=4.74 Hz), 2.68 (d, 2H, —NHCH$_2$CH$_2$CH$_2$C<u>H</u>$_2$—, J=6.52 Hz), 1.81 (t, 4H, —NHCH$_2$C<u>H</u>$_2$C<u>H</u>$_2$CH$_2$—, J=4.98 Hz), 1.44 (t, 3H, —CO$_2$CH$_2$C<u>H</u>$_3$, J=7.09 Hz)

Example 41

Synthesis of 8-Amino-4-(2-chloro-benzylamino)-quinoline-3-carboxylic acid ethyl ester The compound prepared in Example 3 was reacted with 2-chloro-benzylamine according to the method as described in Example 4 and the obtained compound was treated as described in Example 14 to prepare the title compound (yield 83%).
$^1$H NMR (300 MHz, CDCl$_3$): δ=9.32 (S, 1H, —N<u>H</u>CH$_2$—), 9.07 (s, 1H, —N═C<u>H</u>—), 7.58 (m, 1H, aromatic H), 7.43–7.15 (m, 4H, aromatic H), 7.12 (t, 1H, aromatic H, J=8.02 Hz), 6.93 (d, 1H, aromatic H, J=7.49 Hz), 4.98 (d, 2H, —NHC<u>H</u>$_2$—, J=6.29 Hz), 4.98 (br, 2H, —N<u>H</u>$_2$), 4.38 (q, 2H, —CO$_2$C<u>H</u>$_2$CH$_3$), 1.43 (t, 3H, —CO$_2$CH$_2$C<u>H</u>$_3$, J=7.10 Hz)

Example 42

Synthesis of 8-Amino-4-(4-chloro-benzylamino)-quinoline-3-carboxylic acid ethyl ester The compound prepared in Example 3 was reacted with 4-chloro-benzylamine according to the method as described in Example 4 and the obtained compound was treated as described in Example 14 to prepare the title compound (yield 85%).
$^1$H NMR (300 MHz, CDCl$_3$): δ=9.35 (S, 1H, —N<u>H</u>CH$_2$—), 9.06 (s, 1H, —N═C<u>H</u>—), 7.43 (d, 1H, aromatic H, J=8.58 Hz), 7.32 (m, 4H, aromatic H), 7.14 (t, 1H, aromatic H, J=8.01 Hz), 6.94 (d, 1H, aromatic H, J=7.51 Hz), 4.97 (br, 2H, —N<u>H</u>$_2$), 4.94 (d, 2H, —NHC<u>H</u>$_2$, J=5.98 Hz), 4.37 (q, 2H, —CO$_2$C<u>H</u>$_2$CH$_3$), 1.42 (t, 3H, —CO$_2$CH$_2$C<u>H</u>$_3$, J=7.09 Hz)

Example 43

Synthesis of 8-Amino-4-(2,4-dichloro-benzylamino)-quinoline-3-carboxylic acid ethyl ester The compound prepared in Example 3 was reacted with 2,4-dichloro-benzylamine according to the method as described in Example 4 and the obtained compound was treated as described in Example 14 to prepare the title compound (yield 88%).
$^1$H NMR (300 MHz, CDCl$_3$): δ=9.28 (S, 1H, —N<u>H</u>CH$_2$—), 9.07 (s, 1H, —N═C<u>H</u>—), 7.54 (d, 1H, aromatic H, J=8.27 Hz), 7.46 (s, 1H, aromatic H), 7.28 (t, 2H, aromatic H, J=9.23 Hz), 7.12 (t, 1H, aromatic H, J=8.00 Hz), 6.94 (d, 1H, aromatic H, J=7.45 Hz), 4.96 (d, 2H, —NHC<u>H</u>$_2$—, J=6.41 Hz), 4.39 (q, 2H, —CO$_2$C<u>H</u>$_2$CH$_3$), 1.43 (t, 3H, —CO$_2$CH$_2$C<u>H</u>$_3$, J=7.11 Hz)

Example 44

Synthesis of 8-Amino-4-(2,3-dimethoxy-benzylamino)-quinoline-3-carboxylic acid ethyl ester The compound prepared in Example 3 was reacted with 2,3-dimethoxy-benzylamine according to the method as described in Example 4 and the obtained compound was treated as described in Example 14 to prepare the title compound (yield 91%).
$^1$H NMR (300 MHz, CDCl$_3$): δ=9.29 (S, 1H, —N<u>H</u>CH$_2$—), 9.04 (s, 1H, —N═C<u>H</u>—), 7.55 (d, 1H, aromatic H, J=9.28 Hz), 7.11 (m, 3H, aromatic H), 6.92 (m, 2H, aromatic H), 4.99 (d, 2H, —NHC<u>H</u>$_2$—, J=5.92 Hz), 4.35 (q, 2H, —CO$_2$C<u>H</u>$_2$CH$_3$), 3.90 (s, 3H, —OC<u>H</u>$_3$), 3.86 (s, 3H, —OC<u>H</u>$_3$), 1.41 (t, 3H, —CO$_2$CH$_2$C<u>H</u>$_3$, J=7.11 Hz)

Example 45

Synthesis of 8-Amino-4-propylamino-quinoline-3-carboxylic acid ethyl ester

The compound prepared in Example 3 was reacted with propyl amine according to the method as described in Example 4 and the obtained compound was treated as described in Example 14 to prepare the title compound (yield 87%).
$^1$H NMR (300 MHz, CDCl$_3$): δ=9.20 (S, 1H, —N<u>H</u>CH$_2$—), 9.02 (s, 1H, —N═C<u>H</u>—), 7.59 (d, 1H, aromatic H, J=8.59 Hz), 7.17 (t, 1H, aromatic H, J=8.05 Hz), 6.94 (d, 1H, aromatic H, J=7.47 Hz), 4.95 (br, 2H, —N<u>H</u>$_2$), 4.39 (q, 2H, —CO$_2$C<u>H</u>$_2$CH$_3$), 3.80 (q, 2H, —NHC<u>H</u>$_2$CH$_2$CH$_3$), 1.80 (q, 2H, —NHCH$_2$C<u>H</u>$_2$CH$_3$), 1.43 (t, 3H, —CO$_2$CH$_2$C<u>H</u>$_3$, J=7.10 Hz), 1.07 (t, 3H, (q, 2H, —NHCH$_2$CH$_2$C<u>H</u>$_3$, J=7.39 Hz)

Example 46

Synthesis of 8-Amino-4-[2-(2-amino-phenyl)-ethylamino]-quinoline-3-carboxylic acid ethyl ester The compound prepared in Example 3 was reacted with 2-(2-amino-phenyl)-ethylamine according to the method as described in Example 4 and the obtained compound was treated as described in Example 14 to prepare the title compound (yield 91%).
$^1$H NMR (300 MHz, CDCl$_3$): δ=9.15 (S, 1H, —N<u>H</u>CH$_2$—), 9.01 (s, 1H, —N═C<u>H</u>—), 7.52 (d, 1H, aromatic H, J=4.55 Hz), 7.26 (m, 1H, aromatic H), 7.18 (t, 1H, aromatic H, J=8.04 Hz), 6.98 (m, 4H, aromatic H), 4.97 (br, 2H, —$NH_2$), 4.38 (q, 2H, —$CO_2CH_2CH_3$), 4.08 (d, 2H, —$NHCH_2CH_2$—, J=7.29 Hz), 3.03 (t, 2H, —$NHCH_2CH_2$, J=8.04 Hz) 1.43 (t, 3H, —$CO_2CH_2CH_3$, J=7.12 Hz)

Example 47

Synthesis of 8-Amino-4-(3,5-dimethoxy-benzylamino)-quinoline-3-carboxylic acid ethyl ester The compound prepared in Example 3 was reacted with 3,5-dimethoxy-benzylamine according to the method as described in Example 4 and the obtained compound was treated as described in Example 14 to prepare the title compound (yield 87%).
$^1$H NMR (300 MHz, $CDCl_3$): δ=9.32 (S, 1H, —$NHCH_2$—), 9.06 (s, 1H, —N=$CH$—), 7.48 (d, 1H, aromatic H, J=8.52 Hz), 7.12 (t, 1H, aromatic H, J=8.24 Hz), 6.94 (d, 1H, aromatic H, J=7.27 Hz), 6.58 (d, 2H, aromatic H, J=1.93 Hz), 4.97 (br, 2H, —$NH_2$), 4.91 (d, 2H, —NH$CH_2$—, J=6.00 Hz), 4.38 (q, 2H,

Example 48

Synthesis of 8-Amino-4-(4-phenoxy-phenylamino)-quinoline-3-carboxylic acid ethyl ester The compound prepared in Example 3 was reacted with 4-phenoxyaniline according to the method as described in Example 4 and the obtained compound was treated as described in Example 14 to prepare the title compound.

Example 49

Synthesis of 8-Amino-4-o-tolylamino-quinoline-3-carboxylic acid(4-methoxy-phenyl)-amide The compound prepared in Example 4 was reacted with o-toluidine according to the method as described in Example 5 and 6, and the obtained compound was treated with p-anisidine as described in Examples 7 and 14 to prepare the title compound.

Example 50

Synthesis of 8-Amino-4-o-tolylamino-quinoline-3-carboxylic acid(4-isopropyl-phenyl)-amide The compound prepared in Example 4 was reacted with o-toluidine according to the method as described in Examples 5 and 6, and the obtained compound was treated with 4-isopropylaniline as described in Examples 7 and 14 to prepare the title compound.

Example 51

Synthesis of 8-Amino-4o-tolylamino-quinoline-3-carboxylic acid (4-fluoro-phenyl)-amide The compound prepared in Example 4 was reacted with o-toluidine according to the method as described in Examples 5 and 6, and the obtained compound was treated with 4-fluoroaniline as described in Examples 7 and 14 to prepare the title compound.

Example 52

Synthesis of 8-Amino-4-o-tolylamino-quinoline-3-carboxylic acid 4-methoxy-benzylamide The compound prepared in Example 4 was reacted with o-toluidine according to the method as described in Examples and 6, and the obtained compound was treated with 4-methoxy-benzyl amine as described in Examples 7 and 14 to prepare the title compound.
$^1$H NMR ($CDCl_3$): 2.44 (s, 3H) 3.83 (s, 3H) 4.58 (d, J=5 Hz, 2H) 4.98 (br, 2H) 6.50–7.04 (m, 9H) 7.28–7.32 (m, 3H) 8.72 (s, 1H) 10.11 (s, 1H)

Example 53

Synthesis of 8-Amino-4-o-tolylamino-quinoline-3-carboxylic acid 3-fluoro-benzylamide The compound prepared in Example 4 was reacted with o-toluidine according to the method as described in Examples 5 and 6, and the obtained compound was treated with 3-fluoro-benzyl amine as described in Examples 7 and 14 to prepare the title compound.
$^1$H NMR ($CDCl_3$): 2.43 (s, 3H) 4.65 (d, J=6 Hz, 2H) 4.98 (br, 2H) 6.79–7.33 (m, 12H) 8.76 (s, 1H) 10.07 (s, 1H)

Example 54

Synthesis of 8-Amino-4-o-tolylamino-quinoline-3-carboxylic acid (pyridin-2-yl methyl)-amide The compound prepared in Example 4 was reacted with o-toluidine according to the method as described in Examples 5 and 6, and the obtained compound was treated with (2-aminomethyl)pyridin as described in Examples 7 and 14 to prepare the title compound.
$^1$H NMR ($CDCl_3$): 2.43 (s, 3H) 3.80 (s, 3H) 4.63 (d, J=5Hz, 2H) 4.98 (br, 2H) 6.50–7.04 (m, 10H) 7.27–7.30 (m, 2H) 8.75 (s, 1H) 10.11 (s, 1H)

Example 55

Synthesis of 8-Amino-4-o-tolylamino-quinoline-3-carboxylic acid (2-methoxy-ethyl)-amide The compound prepared in Example 4 was reacted with o-toluidine according to the method as described in Example 5 and 6, and the obtained compound was treated with 2-methoxy-ethyl amine as described in Examples 7 and 14 to prepare the title compound.
$^1$H NMR ($CDCl_3$): 2.44 (s, 3H) 4.77 (d, J=4 Hz, 2H) 4.98 (br, 2H) 6.85–7.03 (m, 7H) 7.24–7.33 (m, 2H) 7.71–7.72 (m, 1H) 8.00 (s, 1H) 8.59–8.69 (m, 1H) 8.95 (s, 1H)

Example 56

Synthesis of 8-Amino-4-o-tolylamino-quinoline-3-carboxylic acid isopropylamide The compound prepared in Example 4 was reacted with o-toluidine according to the method as described in Example 5 and 6, and the obtained compound was treated with isopropyl amine as described in Examples 7 and 14 to prepare the title compound.

¹H NMR (CDCl₃): 2.44 (s, 3H) 3.42 (s, 3H) 3.57–3.67 (m, 4H) 4.98 (br, 2H) 6.73–7.02 (m, 7H) 7.24–7.28 (m, 1H) 8.77 (s, 1H) 10.07 (s, 1H)

Example 57

Synthesis of 8-Amino-4-o-tolylamino-quinoline-3-carboxylic acid (3-isopropoxy-propyl)-amide The compound prepared in Example 4 was reacted with o-toluidine according to the method as described in Examples 5 and 6, and the obtained compound was treated with 3-isopropoxy-propyl amine as described in Examples 7 and 14 to prepare the title compound.
¹H NMR (CDCl₃) 1.26–1.31 (m, 3H) 2.45 (s, 1H) 4.25–4.29 (m, 1H) 4.96 (br, 2H) 6.74–7.24 (m, 7H) 7.27–7.28 (m, 1H) 8.72 (s, 1H) 10.03 (s, 1H)

Example 58

Synthesis of 8-Amino-4-[(pyridin-2-ylmethyl)-amino]-quinoline-3-carboxylic acid isobutyl-amide The compound prepared in Example 4 was reacted with (2-aminomethyl)pyridine according to the method as described in Examples 5 and 6, and the obtained compound was treated with isobutyl amine as described in Examples 7 and 14 to prepare the title compound.
¹H NMR (CDCl₃): 1.24–1.28 (m, 6H) 1.90–1.95 (m, 2H) 2.45 (s, 3H) 3.58–3.69 (m, 4H) 4.98 (br, 2H) 6.76–7.01 (m, 6H) 7.25–7.28 (m, 1H) 7.50 (s, 1H) 8.74 (s, 1H) 10.36 (s, 1H)

Example 59

Synthesis of 8-Amino-4-[(pyridin-2-ylmethyl)-amino]-quinoline-3-carboxylic acid allyl ester The compound prepared in Example 4 was reacted with (2-aminomethyl)pyridine according to the method as described in Examples 5 and 6, and the obtained compound was treated with allyl alcohol as described in Examples 7 and 14 to prepare the title compound.
¹H NMR (CDCl₃): 0.99–1.04 (m, 3H) 1.28 (d, J=6 Hz, 3H) 1.58–1.65 (m, 2H) 4.16–4.21 (m, 1H) 4.84–4.92 (m, 4H) 6.14 (d, J=7 Hz, 1H) 6.89 (d, J=7 Hz, 1H) 7.21–7.44 (m, 4H) 7.66–7.71 (m, 1H) 8.37 (s, 1H) 8.64 (s, 1H) 8.65 (s, 1H)

Example 60

Synthesis of 8-Amino-4-[(pyridine-2-ylmethyl)-amino]-quinoline-3-carboxylic acid propyl ester The compound prepared in Example 4 was reacted with (2-aminomethyl)pyridine according to the method as described in Examples 5 and 6, and the obtained compound was treated with propyl alcohol as described in Examples 7 and 14 to prepare the title compound.
¹H NMR (CDCl₃): 4.87–5.14 (m, 6H) 5.33 (d, J=10 Hz, 1H) 5.45 (d, J=45 Hz, 1H) 5.90–6.20 (m, 1H) 6.94 (d, J=8 Hz, 1H) 7.13–7.72 (m, 5H) 8.68 (d, J=1 Hz, 1H) 9.09 (s, 1H) 9.90 (s, 1H)

Example 61

Synthesis of 8-Amino-4-[(pyridin-2-ylmethyl)-amino]-quinoline-3-carboxylic acid isopropyl ester The compound prepared in Example 4 was reacted with (2-aminomethyl)pyridine according to the method as described in Examples 5 and 6, and the obtained compound was treated with isopropyl alcohol as described in Examples 7 and 14 to prepare the title compound.
¹H NMR (CDCl₃): 1.07 (t, J=7 Hz, 3H) 1.80–1.87 (m, 2H) 4.32 (t, J=6 Hz, 2H) 4.98 (br, 2H) 5.13 (d, J=6 Hz, 2H) 6.93 (d, J=1 Hz, 1H) 6.95–7.72 (m, 5H) 8.68 (s, 1H) 9.07 (s, 1H) 9.84 (s, 1H)

Example 62

Synthesis of 8-Amino-4-[(pyridine-2ylmethyl)-amino]-quinoline-3-carboxylic acid 4-fluoro-benzyl ester The compound prepared in Example 4 was reacted with (2-aminomethyl)pyridine according to the method as described in Examples 5 and 6, and the obtained compound was treated with 4-fluoro-benzyl alcohol as described in Examples 7 and 14 to prepare the title compound.
¹H NMR (CDCl₃): 1.27–1.44 (m, 6H) 4.98 (br, 2H) 5.13 (d, J=6 Hz, 1H) 5.28–5.32 (m, 1H) 6.93 (d, J=1 Hz, 1H) 6.95–7.72 (m, 10H) 8.68 (s, 1H) 9.07 (s, 1H) 9.84 (s, 1H)

Example 63

Synthesis of 8-Amino-4-[(pyridine-2ylmethyl)-amino]-quinoline-3-carboxylic acid 3-methyl-benzyl ester The compound prepared in Example 4 was reacted with (2-aminomethyl)pyridine according to the method as described in Examples 5 and 6, and the obtained compound was treated with 3-methyl-benzyl alcohol as described in Examples 7 and 14 to prepare the title compound.
¹H NMR (CDCl₃): 4.98 (br, 2H) 5.13 (d, J=6 Hz, 2H) 5.38 (s, 2H) 6.94–7.72 (m, 10H) 8.69 (d, J=5 Hz, 1H) 9.08 (s, 1H) 9.84 (s, 1H)

Example 64

Synthesis of Propane-1-sulfonic acid [8-amino-4-(3-morpholin-4-yl-propylamino)-quinoline-3-yl]-amide The compound prepared in Example 4 was reacted with 3-morpholin-4-yl-propyl amine according to the method as described in Examples 5 and 8, and the obtained compound was treated with 1-propanesulfonyl chloride as described in Examples 9 and 15 to prepare the title compound.
¹H NMR (CDCl₃): 4.98 (br, 2H) 5.14 (d, J=6 Hz, 2H) 5.46 (s, 2H) 6.96 (d, J=5 Hz, 1H) 7.15–7.74 (m, 9H) 8.69 (d, J=5 Hz, 1H) 9.10 (s, 1H) 9.85 (s, 1H)

Example 65

Synthesis of N-[8-Amino-4-(3-morpholin-4-yl-propylamino)-quinoline-3-yl]-3-bromo-benzenesulfonamide The compound prepared in Example 4 was reacted with 4-(3-aminopropyl)morpholine according to the method as described in Examples 5 and 8, and the obtained compound was treated with 3-bromo-benzene sulfonyl chloride as described in Examples 9 and 15 to prepare the title compound.

$^1$H NMR (CDCl$_3$): 2.62 (t, J=7 Hz, 3H) 3.15 (s, 2H) 3.42–3.49 (m, 2H) 3.59–3.63 (m, 2H) 3.99–4.08 (m, 6H) 5.23–5.28 (m, 4H) 5.95–6.00 (m, 2H) 6.71 (s, 2H) 8.45–8.48 (m, 1H) 8.81 (s, 1H) 8.90–9.03 (m, 2H) 10.76 (s, 1H)

Example 66

Synthesis of naphthalene-1-sulfonic acid [8-amino-4-(3-morpholin-4-yl-propylamino)-quinoline-3-yl]-amide The compound prepared in Example 4 was reacted with 4-(3-aminopropyl)morpholine according to the method as described in Examples 5 and 8, and the obtained compound was treated with 1-naphthalenesulfonyl chloride as described in Examples 9 and 15 to prepare the title compound.

$^1$H NMR (CDCl$_3$): 2.04–2.16 (m, 2H) 2.58 (s, 6H) 3.76 (s, 4H) 4.33 (t, J=9 Hz, 2H) 5.18 (s, 2H) 6.90–6.93 (m, 1H) 7.28–7.73 (m, 5H) 8.18 (d, J=9 Hz, 2H) 9.39 (s, 1H)

Example 67

Synthesis of 4-Amino-N-[8-amino-4-(3-morpholin-4-yl-propylamino)-quinoline-3-yl]-benzenesulfonamide The compound prepared in Example 4 was reacted with 4-(3-aminopropyl)morpholine according to the method as described in Examples 5 and 8, and the obtained compound was treated with 4-amino-benzenesulfonyl chloride as described in Examples 9 and 15 to prepare the title compound.

$^1$H NMR (CDCl$_3$): 1.88–1.93 (m, 2H) 2.26–2.33 (m, 6H) 3.59 (s, 4H) 4.24 (t, J=7 Hz, 2H) 5.20 (br, 2H) 6.93 (t, J=7 Hz, 1H) 7.28–8.21 (m, 8H) 8.58–8.61 (m, 1H) 8.74 (d, J=7 Hz, 1H) 9.56 (s, 1H)

Example 68

Synthesis of N-[8-amino-4-(2-pyridin-2-yl-ethylamino)-quinoline-3-yl]-benzenesulfonamide The compound prepared in Example 4 was reacted with 2-pyridin-2-yl-ethylamine according to the method as described in Examples 5 and 8, and the obtained compound was treated with benzenesulfonyl chloride as described in Examples 9 and 15 to prepare the title compound.

$^1$H NMR (DMSO-d$_6$): 1.80–1.83 (m, 2H) 2.09–2.21 (m, 6H) 3.27–3.39 (m, 8H) 4.24 (s, 2H) 6.09 (s, 2H) 6.45–6.87 (m, 3H) 7.34 (s, 2H) 7.68 (d, J=9 Hz, 1H) 9.16 (s, 1H)

Example 69

Synthesis of 8-Amino-4-(3-morpholin-4-yl-propylamino)-quinoline-3-carbonitrile

The compound prepared in Example 12 was reacted with 4-(3-aminopropyl)morpholine according to the method as described in Example 12 and the obtained compound was treated as described in Examples 13 and 16 to prepare the title compound.

$^1$H NMR (CDCl$_3$): 3.29 (t, J=8 Hz, 2H) 4.65 (t, J=8 Hz, 2H) 6.91–7.70 (m, 10H) 8.18 (d, J=8 Hz, 2H) 8.49 (d, J=7 Hz, 1H) 9.41 (s, 1H)

Example 70

Synthesis of 8-Amino-4-phenylamino-quinoline-3-carbonitrile

The compound prepared in Example 12 was reacted with phenyl amine according to the method as described in Example 12 and the obtained compound was treated as described in Examples 13 and 16 to prepare the title compound.

$^1$H NMR (CDCl$_3$): 1.95–2.01 (m, 2H) 2.62–2.69 (m, 6H) 3.81–3.90 (m, 4H) 4.07–4.12 (m, 2H) 4.97 (s, 2H) 6.94–6.97 (m, 1H) 7.28–7.31 (m, 2H) 8.09 (s, 1H) 8.44 (s, 1H)

Example 71

Synthesis of 8-Amino-4-(2-pyridin-2-yl-ethylamino)-quinoline-3-carbonitrile

The compound prepared in Example 12 was reacted with 2-pyridin-2-yl ethyl amine according to the method as described in Example 12 and the obtained compound was treated as described in Examples 13 and 16 to prepare the title compound.

$^1$H NMR (CDCl$_3$): 5.32 (br, 2H) 6.99–7.46 (m, 9H) 8.58 (s, 1H)

Example 72

Synthesis of 8-Amino-4-(3-isopropoxy-propylamino)-quinoline-3-carbonitrile

The compound prepared in Example 12 was reacted with 3-isoproxy propyl amine according to the method as described in Example 12 and the obtained compound was treated as described in Examples 13 and 16 to prepare the title compound.

$^1$H NMR (CDCl$_3$): 3.25 (t, J=6 Hz, 2H) 4.29–4.34 (m, 2H) 6.95 (t, J=5 Hz, 1H) 7.23–7.36 (m, 4H) 7.68–7.74 (m, 1H) 8.10 (s, 1H) 8.63 (s, 1H) 8.65 (s, 1H)

Example 73

N-[8-Amino-4-(3-morpholin-4-yl-propylamino)-quinoline-3-yl]-C-(2-amino-phenyl)-methansulfonamide The compound prepared in Example 4 was reacted with benzylamine according to the method as described in Examples 5 and 8, and the obtained compound was treated with 2-amino-α-toluenesulfonyl chloride as described in Examples 9 and 15 to prepare the title compound.

$^1$H NMR (CDCl$_3$): 1.26–1.28 (m, 6H) 2.05–2.09 (m, 2H) 3.66–3.78 (m, 3H) 4.07–4.11 (m, 2H) 4.98 (br, 2H) 6.93–7.28 (m, 4H) 8.44 (s, 1H)

According to the method described in the above Examples, 8-Amino-4-(2-amino-benzylamino)-quinoline-3-carboxylic acid ethyl ester, 8-Amino-4-(3-morpholin-4-yl-propyl amino)-quinoline-3-carboxylic acid propenyl ester, and 8-Amino-4-(3-morpholin-4-yl-propyl amino)-quinoline-3-carboxylic acid propyl ester were prepared.

EXPERIMENTAL EXAMPLES

Example A

Assay of Caspase Inhibitory Activity

Example A. 1

Preparation of Human Recombinant Caspase-3 Enzyme

The active form of human recombinant caspase-3 enzyme was prepared from *Escherichia coli* (*E.coli*) heterologous expression system as described previously (Rotonda J. et al., Nat Struct Biol 3(7): 617–25, 1996). Briefly, each cDNA encoding p12 and p17 subunits of caspase-3 was PCR-amplified respectively and subcloned into a pET3-a expression vector (Novagen), which was followed by transfection into *E. coli* strain BL21 (DE3). The bacterial cultures (0.5 liters for each transfectant) were grown at 37° C. until logarithmic phase of cell growth and isopropyl-1-thio-β-D-galactopyranoside (IPTC) (Pharmacia) was then added to a final concentration of 0.5 mM. After 3 hr of incubation, the bacteria were pelleted and lysed in a lysis buffer (20 mM Tris hydrochloride pH 8.0, 1 mM EDTA, 2 mM dithiothreitol (DTT), 100 mM NaCl, 200 ug/ml of lysozyme) through sonication. After centrifugation, the pellets from each transfectants were dissolved in 6 M urea and were mixed and rapidly diluted 50 fold in 100 mM HEPES/KOH (pH 7.5), 10% sucrose, 0.1% CHAPS, 0.5 M NaCl, 10 mM DTT. The concentration of protein was determined with the Bradford method (Bio-Rad), with bovine serum albumin as the standard. To verify whether expected size of proteins were obtained, the cell lysates from each cDNA transfectants were analyzed on 14% SDS PAGE and visualized with Coomassie blue staining.

Example A. 2

Enzyme Assay of Caspase-3 Inhibition 200 ul of the following assay solution was contained in each well of 96-well plate: 20 mM HEPES/KOH (pH 7.5), 10% sucrose, 10 mM DTT, 0.2 mM EDTA, 0.1% CHAPS, 200 ng of enzymes, and 2.5 uM of the substrate. The fluorogenic substrate benzyloxycarbonyl-Asp-Glu-Val-Asp-7-amino-4-trifluoromethylcoumarin (Ac-DEVD-AFC) was purchased from Sigma (St Louis, Mo.) and dissolved in DMSO as a 2.5 mM stock solution and kept at −20° C. before use.

After 1 hr incubation at 37° C., the release of AFC (7-amino-4-trifluoromethyl-coumarin) was monitored in a fluorometric plate reader (Victor 1420). The excitation and emission wavelengths were 400 nm and 510 nm, respectively. The inhibitory effects of compounds on enzyme activities were determined with 2, 20 or 200 uM concentrations of the test compound run in triplicate tubes, and isotherms from three assays were calculated by computerized nonlinear regression analysis (GraphPad Prism Program, San Diego, Calif.) to yield $IC_{50}$ values.

TABLE 1

| Example No. | $IC_{50}$ | %-Inhibition | Example No. | $IC_{50}$ | %-Inhibition* |
|---|---|---|---|---|---|
| 17 | 14.4 | 81.7 | 33 | 15.8 | 86.5 |
| 18 | 14.1 | 84.7 | 34 | 16 | 83.9 |
| 19 | 14.9 | 84.9 | 35 | 13.6 | 91.5 |
| 20 | 13.2 | 90.1 | 37 | 15.3 | 82.1 |
| 21 | 19.2 | 78.0 | 38 | 16.6 | 77.2 |
| 22 | 13.8 | 92.3 | 39 | 16.4 | 78.8 |
| 23 | 14.3 | 86.0 | 40 | 16.4 | 81.7 |
| 25 | 16.5 | 88.8 | 41 | 17.8 | 78.4 |
| 26 | 15.4 | 88.9 | 42 | 17 | 82.9 |
| 27 | 15.9 | 87.8 | 43 | 27 | 54.7 |
| 28 | 17.6 | 85.2 | 44 | 18.1 | 72.1 |
| 29 | 18.8 | 78.8 | 45 | 16 | 85.0 |
| 30 | 19.1 | 76.9 | 46 | 16.2 | 83.8 |
| 31 | 13.5 | 92.5 | 47 | 21.2 | 69.3 |
| 32 | 16.9 | 82.9 | 60 | | 76.8 |
| 61 | | 81.4 | | | |

*%-inhibition at 20 uM

Meanwhile, the reference compound, (S)-1-methyl-5-{1-[2-(phenoxymethyl)pyrrolidinyl]sulfonyl} isatin (GlaxoSmithKline) inhibited 76.8% of caspase-3 activity at 20 uM.

The compounds in the above table showed effective inhibitory activity against caspase-3 compared to the reference compound. Specifically, 8-amino-4-[(pyridine-2-ylmethyl)-amino]-quinoline-3-carboxylic acid ethylester, 8-amino-4-(3-morpholine-4-yl-propylamino)-quinoline-3-carboxylic acid ethylester, 8-amino-4-(3-isopropoxy-propylamino)-quinoline-3-carboxylic acid ethylester and 8-amino-4-(2-methoxy-ethylamino)-quinoline-3-carboxylic acid ethylester showed superior activity.

Example B

Assay of Selective Inhibitory Activity

To investigate the selectivity on caspase enzyme subtypes, the inhibitory effects of the compounds of this invention on several other members of the caspase family, caspase-1, 6, 7 and 8 were evaluated.

After 1 hr incubation at 37° C., the release of AFC (7-amino-4-trifluoromethyl-coumarin) was monitored in a fluorometric plate reader (Victor 1420). The excitation and emission wavelengths were 400 nm and 510 nm, respectively. Isotherms from three assays were calculated by computerized nonlinear regression analysis (GraphPad Prism Program, San Diego, Calif.) to yield $IC_{50}$ values. Caspase-1, 6, 7 and 8 were purchased from BIOMOL Research Laboratories Inc. (Plymouth Meeting, Pa., USA).

Coumarin-based fluorogenic substrates for each enzyme were obtained from Sigma/RBI (St. Louis, Mo., USA). The compound used in the assay was 8-amino-4-(3-morpholine-4-yl-propylamino)-quinoline-3-carboxylic acid ethyl ester. The enzymatic activity of caspase-1, 6, 7 or 8 was determined by the same procedures as for the caspase-3 assay, except for enzyme or substrate (Table 2).

TABLE 2

| | Caspase-1 | Caspase-6 | Caspase-7 | Caspase-8 |
|---|---|---|---|---|
| Enzyme source | Human recombinant, expressed in *E. coli.* (50 U) | Human recombinant, expressed in *E. coli.* (30 U) | Human recombinant, expressed in *E. coli.* (40 ng) | Human recombinant, expressed in *E. coli.* (50 ng) |
| Substrate* | Ac-YVAD-AFC* (200 uM) | Ac-VEID-AFC** (200 uM) | Ac-DEVD-AFC*** (200 uM) | Ac-AEVD-AFC**** (200 uM) |
| Assay buffer | 50 mM HEPES (pH 7.4) containing 100 mM NaCl, 0.1% CHAPS, 1 mM EDTA, 10% glycerol and 10 mM DTT | | | |

*Ac-YVAD-AFC;
N-acetyl-Tyr-Val-Ala-Asp-7-amido-4-trifluoromethylcoumarin
**Ac-VEID-AFE;
N-acetyl-Val-Glu-Ile-Asp-7-amido-4-trifluoromethylcoumarin
***Ac-DEVD-AFC;
N-acetyl-Asp-Glu-Val-Asp-7-amido-4-trifluoromethylcoumarin
****Ac-AEVD-AFC;
N-acetyl-Ala-Glu-Val-Asp-7-amido-4-trifluoromethylcoumarin As a result, $IC_{50}$ values of the compound of this invention were found to be 200 uM or more, 5.6 uM, 200 uM or more, 14.7 uM and 200 uM or more against caspase-1, 3, 6, 7 and 8, respectively. In view of this result, it was confirmed that the compounds of this invention show selective inhibitory activity against caspase-3.

INDUSTRIAL APPLICATION

The novel quinoline derivative or its pharmaceutically acceptable salt of this invention is effective for the treatment of caspase-associated diseases by inhibiting the activity of caspase-3 such as Alzheimer's disease, Huntington's disease, Parkinson's disease, ALS, AIDS, stroke/ischemia, traumatic brain injury, spinal cord injury, osteoarthritis and etc.

What is claimed is:

1. A quinoline derivative of formula 1 or its pharmaceutically acceptable salt:

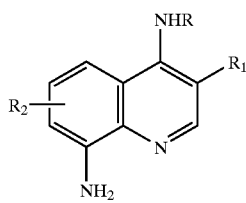

Formula 1 wherein $R_2$ is H; halogen; $C_{1-6}$ alkyl; $C_{1-6}$ alkoxy; $C_{1-6}$ alkoxyalkyl; or $C_{3-6}$ cycloalkyl;

$R_1$ is

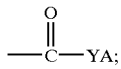

—CN; or wherein Y is O; N; or S;

A is H; $C_{3-6}$ alkenyl unsubstituted or substituted by $C_{1-3}$ alkyl; $C_{3-6}$ cycloalkyl; $C_{6-14}$ aryl unsubstituted or substituted by halogen, $C_{1-6}$ alkyl or $C_{1-6}$ alkoxy; $C_{1-6}$ alkoxyalkyl; or $C_{1-6}$ alkyl unsubstituted or substituted by $C_{6-14}$ aryl or 5–15 membered heteroaryl wherein aryl group can be unsubstituted or substituted by halogen, $C_{1-6}$ alkyl, $C_{1-6}$ halogenoalkyl, $C_{1-6}$ alkoxy or amino group;

$R_3$ is H; halogen; unsubstituted or substituted amino; $C_{1-6}$ alkyl; $C_{1-6}$ alkoxy; $C_{1-6}$ alkoxyalkyl; or $C_{3-6}$ cycloalkyl;

n is 0, 1, 2 or 3;

R is H; $C_{6-14}$ aryl unsubstitued or substituted by halogen, $C_{1-6}$ alkyl, $C_{1-6}$ alkoxy or amino; 5–15 membered heterocyclic group unsubstituted or substituted by halogen, $C_{1-6}$ alkyl, $C_{1-6}$ alkoxy or amino; or —(CH$_2$)$_n$—CHR$_4$R$_5$ wherein n is 0, 1, 2, 3 or 4;

$R_4$ is H; $C_{1-6}$ alkyl; $C_{1-6}$ alkoxy; $C_{6-14}$ aryl unsubstitued or substituted by halogen, $C_{1-6}$ alkyl, $C_{1-6}$ halogenoalkyl, $C_{1-6}$ alkoxy or amino; 5–15 membered heteroaryl; $C_{3-6}$ cycloalkyl; 5–15 membered heterocyclic group unsubstituted or substituted by $C_{1-6}$ alkyl; or 5–15 membered $C_{6-14}$ aryl fused to heterocyclic group;

$R_5$ is H; $C_{1-6}$ alkyl; $C_{1-6}$ alkoxy; or $C_{1-6}$ alkoxyalkyl.

2. The compound of claim 1 where $R_2$ is H; halogen; $C_{1-6}$ alkyl; $C_{1-6}$ alkoxy; $C_{1-6}$ alkoxyalkyl; or $C_{3-6}$ cycloalkyl;

$R_1$ is

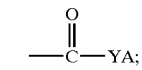

—CN; or

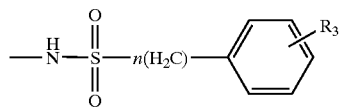

wherein Y is O; or N;

A is H; $C_{3-6}$ alkenyl; $C_{3-6}$ cycloalkyl; $C_{6-14}$ aryl unsubstituted or substituted by halogen, $C_{1-6}$ alkyl or $C_{1-6}$ alkoxy; $C_{1-6}$ alkoxyalkyl; or $C_{1-6}$ alkyl unsubstituted or substituted by $C_{6-14}$ aryl or 5–15 membered heteroaryl wherein the aryl group can be unsubstituted or substituted by halogen, $C_{1-6}$ alkyl, $C_{1-6}$ halogenoalkyl, $C_{1-6}$ alkoxy or amino group;

$R_3$ is H; halogen; unsubstituted or substituted amino; $C_{1-6}$ alkyl; $C_{1-6}$ alkoxy; $C_{1-6}$ alkoxyalkyl; or $C_{3-6}$ cycloalkyl;

n is 0, 1, 2 or 3;

R is H; $C_{6-14}$ aryl substituted by $C_{1-6}$ alkyl; 5–15 membered heterocyclic group substituted by $C_{1-6}$ alkyl; or —$(CH_2)_n$—$CHR_4R_5$ wherein n is 0, 1, 2, 3 or 4;

$R_4$ is H; $C_{1-6}$ alkyl; $C_{1-6}$ alkoxy; $C_{6-14}$ aryl unsubstituted or substituted by halogen, $C_{1-6}$ alkyl, $C_{1-6}$ halogenoalkyl, $C_{1-6}$ alkoxy or amino; 5–15 membered heteroaryl; $C_{3-6}$ cycloalkyl; 5–15 membered heterocyclic group; or $C_{6-14}$ aryl fused to 5–15 membered heterocyclic group;

$R_5$ is H; $C_{1-6}$ alkyl; $C_{1-6}$ alkoxy; or $C_{1-6}$ alkoxyalkyl.

3. The compound of claim 1 where the compound of formula 1 is $R_2$ is H;

$R_1$ is

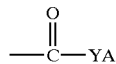

wherein Y is O;

A is H; $C_{3-6}$ alkenyl; or $C_{1-6}$ alkyl;

R is H; or —$(CH_2)_n$—$CHR_4R_5$ wherein n is 0, 1, 2 or 3;

$R_4$ is H; $C_{1-6}$ alkyl; $C_{1-6}$ alkoxy; $C_{6-14}$ aryl unsubstituted or substituted by halogen, $C_{1-6}$ alkyl, $C_{1-6}$ halogenoalkyl, $C_{1-6}$ alkoxy or amino; 5–15 membered heteroaryl; $C_{3-6}$ cycloalkyl; 5–15 membered heterocyclic group; or $C_{6-14}$ aryl fused to 5–15 membered heterocyclic group;

$R_5$ is H; $C_{1-6}$ alkyl; or $C_{1-6}$ alkoxyalkyl.

4. The compound of claim 1 where $R_2$ is H;

$R_1$ is

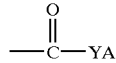

wherein Y is O; A is ethyl; or propenyl;

R is H; or —$(CH_2)_n$—$CHR_4R_5$ wherein n is 1, 2, 3 or 4; $R_4$ is methyl, ethyl, propyl, butyl or isobutyl; methoxy or ethoxy; phenyl or napthyl unsubstitued or substituted by chlorine, fluorine, methyl, methoxy, trifluoromethyl or amino; pyridyl; hexyl; morpholyl; thiopenyl; or benzo-dioxol; $R_5$ is H; methyl, ethyl, propyl, isopropyl, butyl or isobutyl; or methoxymethyl.

5. The compound of claim 1 where the compound is selected from group of consisting of:
  8-amino-4-benzylamino-quinoline-3-carboxylic acid ethyl ester,
  8-amino-4-cyclohexylamino-quinoline-3-carboxylic acid ethyl ester,
  8-amino-4-[(naphthalene-1-ylmethyl)-amino]-quinoline-3-carboxylic acid ethyl ester,
  8-amino-4-[(pyridine-2-ylmethyl)-amino]-quinoline-3-carboxylic acid ethyl ester,
  8-amino-4-[(thiopen-2-ylmethyl)-amino]-quinoline-3-carboxylic acid ethyl ester,
  8-amino-4-(3-morpholine-4-yl-propylamino)-quinoline-3-carboxylic acid ethyl ester,
  8-amino-4-[(benzo[1,3]-dioxol-5-ylmethyl)-amino]-quinoline-3-carboxylic acid ethyl ester,
  8-amino-4-(3-trifluoromethyl-benzylamino)-quinoline-3-carboxylic acid ethyl ester,
  8-amino-4-(1-methoxymethyl-propylamino)-quinoline-3-carboxylic acid ethyl ester,
  8-amino-4-butylamino-quinoline-3-carboxylic acid ethyl ester,
  8-amino-4-isobutylamino-quinoline-3-carboxylic acid ethyl ester,
  8-amino-4-isopropylamino-quinoline-3-carboxylic acid ethyl ester,
  8-amino-4-(2-fluoro-benzylamino)-quinoline-3-carboxylic acid ethyl ester,
  8-amino-4-(3-fluoro-benzylamino)-quinoline-3-carboxylic acid ethyl ester,
  8-amino-4-(3-isopropoxy-propylamino)-quinoline-3-carboxylic acid ethyl ester,
  8-amino-4-(2-methoxy-benzylamino)-quinoline-3-carboxylic acid ethyl ester,
  8-amino-4-(4-methoxy-benzylamino)-quinoline-3-carboxylic acid ethyl ester,
  8-amino-4-(3-methoxy-benzylamino)-quinoline-3-carboxylic acid ethyl ester,
  8-amino-4-(2-methoxy-ethylamino)-quinoline-3-carboxylic acid ethyl ester,
  8-amino-4-(4-methyl-benzylamino)-quinoline-3-carboxylic acid ethyl ester,
  8-amino-4-phenethylamino-quinoline-3-carboxylic acid ethyl ester,
  8-amino-4-(3-phenyl-propylamino)-quinoline-3-carboxylic acid ethyl ester,
  8-amino-4-(4-phenyl-butylamino)-quinoline-3-carboxylic acid ethyl ester,
  8-amino-4-(2-chlorobenzylamino)-quinoline-3-carboxylic acid ethyl ester,
  8-amino-4-(4-chloro-benzylamino)-quinoline-3-carboxylic acid ethyl ester,
  8-amino-4-propylamino-quinoline-3-carboxylic acid ethyl ester,
  8-amino-4-[2-(2-aminophenyl)-ethylamino]-quinoline-3-carboxylic acid ethyl ester,
  8-amino-4-(2-amino-benzylamino)-quinoline-3-carboxylic acid ethyl ester,
  8-amino-4-(3-morpholine-4-yl-propylamino)-quinoline-3-carboxylic acid propenyl ester,
  8-amino-4-(3-morpholine-4-yl-propylamino)-quinoline-3-carboxylic acid propyl ester,
  8-amino-4-[(pyridine-2-ylmethyl)-amino]-quinoline-3-carboxylic acid propyl ester, and their pharmaceutically acceptable salts.

6. The compound of claim 1 where the compound is selected from the group consisting of 8-amino-4-[(pyridine-2-ylmethyl)-amino]-quinoline-3-carboxylic acid ethyl ester, 8-amino-4-(3-morpholine-4-yl-propylamino)-quinoline-3-carboxylic acid ethyl ester, 8-amino-4-(3-isopropoxy-propylamino)-quinoline-3-carboxylic acid ethyl ester, 8-amino-4-(2-methoxy-ethylamino)-quinoline-3-carboxylic acid ethyl ester, and their pharmaceutically acceptable salts.

7. A method for preparing the compound of formula 1a

Formula 1a

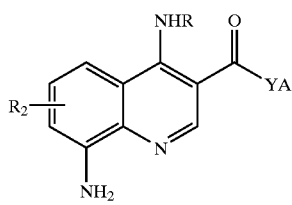

wherein

Y is O; or N;

A is H; $C_{3-6}$ alkenyl; $C_{3-6}$ cycloalkyl; $C_{6-14}$ aryl unsubstituted or substituted by halogen, $C_{1-6}$ alkyl or $C_{1-6}$ alkoxy; $C_{1-6}$ alkoxyalkyl; or $C_{1-6}$ alkyl unsubstituted or substituted by $C_{6-14}$ aryl or 5–15 membered heteroaryl wherein the aryl group can be unsubstituted or substituted by halogen, $C_{1-6}$ alkyl, $C_{1-6}$ halogenoalkyl, $C_{1-6}$ alkoxy or amino group;

R is H; $C_{6-14}$ aryl substituted by $C_{1-6}$ alkyl; 5–15 membered heterocyclic group substituted by $C_{1-6}$ alkyl; or —$(CH_2)_n$—$CHR_4R_5$ wherein n is 0, 1, 2, 3 or 4;

$R_4$ is H; $C_{1-6}$ alkyl; $C_{1-6}$ alkoxy; $C_{6-14}$ aryl unsubstituted or substituted by halogen, $C_{1-6}$ alkyl, $C_{1-6}$ halogenoalkyl, $C_{1-6}$ alkoxy or amino; 5–15 membered heteroaryl; $C_{3-6}$ cycloalkyl; 5–15 membered heterocyclic group; or $C_{6-14}$ aryl fused to 5–15 membered heterocyclic group;

$R_5$ is H; $C_{1-6}$ alkyl; $C_{1-6}$ alkoxy; or $C_{1-6}$ alkoxyalkyl; and $R_2$ is H; halogen; $C_{1-6}$ alkyl; $C_{1-6}$ alkoxy; $C_{1-6}$ alkoxyalkyl; or $C_{3-6}$ cycloalkyl; or its pharmaceutically acceptable salt which is characterized by comprising the steps of:

1) reacting the compound of formula 2

Formula 2

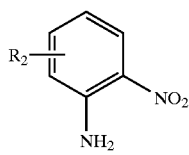

with the compound of formula 3

Formula 3

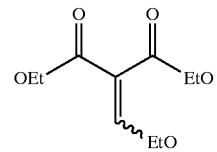

without solvent at 100 to 150° C. with heating or with organic solvent at its boiling point to obtain the compound of formula 4

Formula 4

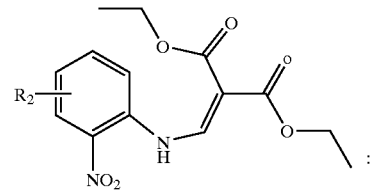

2) cyclizing the compound of formula 4 in organic solvent at 200° C. to the boiling point of the solvent with heating to obtain the compound of formula 5

Formula 5

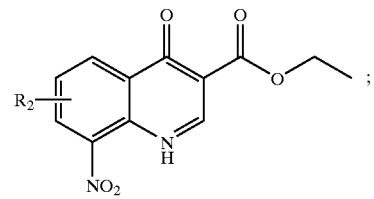

3) reacting the compound of formula 5 with phosphorous oxychloride, phosphorous trichloride or phosphorous pentachloride to obtain the compound of formula 6

Formula 6

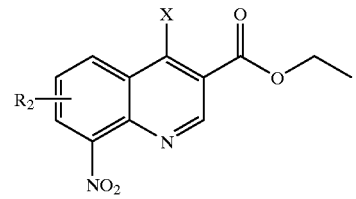

wherein X is halogen, or reacting the compound of formula 5 with sulphonylchloride or phosphorylchloride in organic solvent with the addition of base at −10 C° to ambient temperature to obtain the compound of formula 6 wherein X is sulphonate or phosphonate;

4) reacting the compound of formula 6 with the amine of formula 7

RNH$_2$    Formula 7 in organic solvent at ambient temperature to the boiling point of the solvent to obtain the compound of formula 8

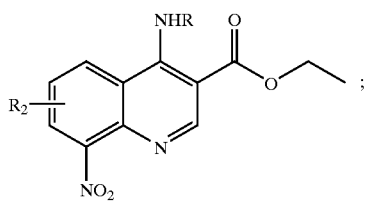

Formula 8

5) hydrolyzing the compound of formula 8 with base in the solvent mixture of organic solvent and water to obtain the compound of formula 9

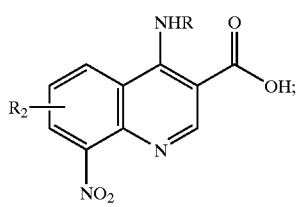

Formula 9

6) reacting the compound of formula 9 with thionylchloride, sulphonylchloride or phosphorylchloride in organic solvent with the addition of base at −10- to ambient temperature to obtain the compound of formula 10

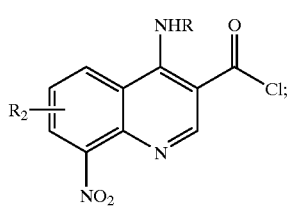

Formula 10

7) reacting the compound of formula 10 with a compound of formulas 11a–c

HOA                  Formula 11a

H$_2$NA               Formula 11b

HAS                 Formula 11c wherein A is H; C$_{3-6}$ alkenyl; or C$_{1-6}$ alkyl;

in organic solvent at ambient temperature to the boiling point of the solvent to obtain the compound of formula 12

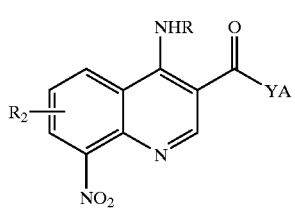

Formula 12 and 8) reducing the compound of formula 12 with the metal catalyst and hydrogen gas in organic solvent at ambient temperature to obtain the compound of formula 1a.

8. A method for preparing the compound of formula 1b

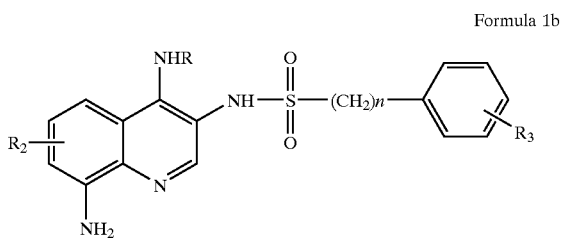

Formula 1b wherein n is 0, 1, 2, or 3;

R$_2$ is H; halogen; C$_{1-6}$ alkyl; C$_{1-6}$ alkoxy; C$_{1-6}$ alkoxyalkyl; or C$_{3-6}$ cycloalkyl;

R$_3$ is H; halogen; unsubstituted or substituted amino; C$_{1-6}$ alkyl; C$_{1-6}$ alkoxy; C$_{1-6}$ alkoxyalkyl; or C$_{3-6}$ cycloalkyl;

R is H; C$_{6-14}$ aryl unsubstitued or substituted by halogen, C$_{1-6}$ alkyl, C$_{1-6}$ alkoxy or amino; 5 . 15 membered heterocyclic group unsubstituted or substituted by halogen, C$_{1-6}$ alkyl, C$_{1-6}$ alkoxy or amino; or —(CH$_2$)$_n$—CHR$_4$R$_5$ wherein is 0, 1, 2, 3 or 4;

R$_4$ is H; C$_{1-6}$ alkyl; C$_{1-6}$ alkoxy; C$_{6-14}$ aryl unsubstitued or substituted by halogen, C$_{1-6}$ alkyl, C$_{1-6}$ halogenoalkyl, C$_{1-6}$ alkoxy or amino; 5–5 membered heteroaryl; C$_{3-6}$ cycloalkyl; 5–5 membered heterocyclic group unsubstituted or substituted by C$_{1-6}$ alkyl; or 5–15 membered C$_{6-14}$ aryl fused to heterocyclic group;

R$_5$ is H; C$_{1-6}$ alkyl; C$_{1-6}$ alkoxy; or C$_{1-6}$ alkoxyalkyl, or its pharmaceutically acceptable salt which is characterized by comprising the steps of:

1) reacting the compound of formula 2

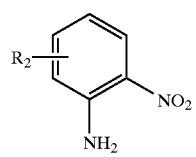

Formula 2 with the compound of formula 3

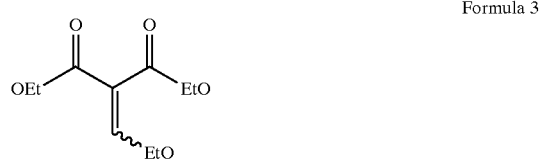

Formula 3 without solvent at 100 to 150 C° with heating or with organic solvent at its boiling point to obtain the compound of formula 4

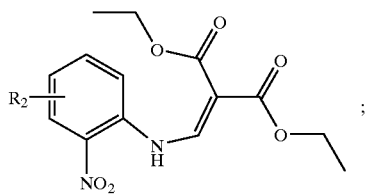

Formula 4

2) cyclizing the compound of formula 4 in organic solvent at 200 C° to the boiling point of the solvent with heating to obtain the compound of formula 5

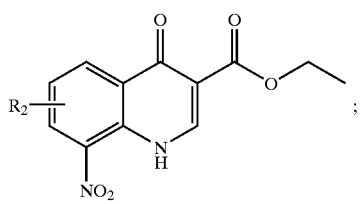

Formula 5

3) reacting the compound of formula 5 with phosphorous oxychloride, phosphorous trichloride, or phosphorous pentachloride to obtain the compound of formula 6

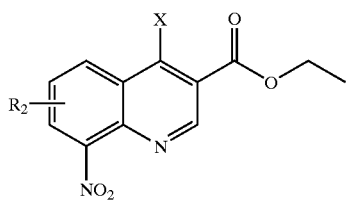

Formula 6 wherein X is halogen, or reacting the compound of formula 5 with sulphonylchloride or phosphorylchloride in organic solvent with the addition of base at −10 C° to ambient temperature to obtain the compound of formula 6 wherein X is sulphonate or phosphonate;

4) reacting the compound of formula 6 with the amine of formula 7

$RNH_2$            Formula 7 in organic solvent at ambient temperature to the boiling poing of the solvent to obtain the compound of formula 8

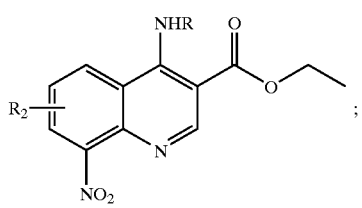

Formula 8

5) hydrolyzing the compound of formula 8 with base in the solvent mixture of organic solvent and water to obtain the compound of formula 9

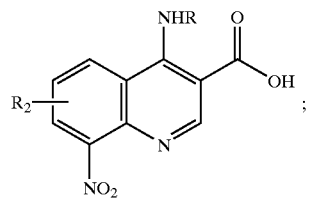

Formula 9

6) reacting the compound of formula 9 for Curtius rearrangement with sodium azide or diphenylphosphorylazide and amine in organic solvent at the boiling point of the solvent to obtain the compound of formula 13

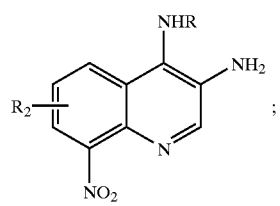

Formula 13

7) reacting the compound of formula 13 with the substituted sulphonylchloride compound of formula 14

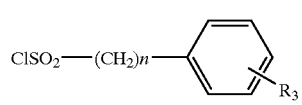

Formula 14 in organic solvent at ambient temperature to the boiling point of the solvent to obtain the compound of formula 15

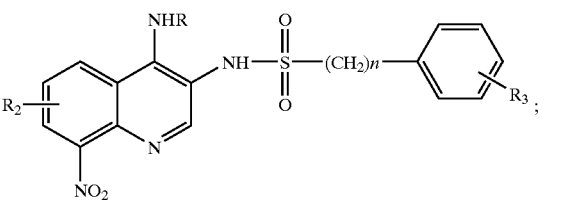

Formula 15

8) reducing the compound of formula 15 with the metal catalyst and hydrogen gas in organic solvent at ambient temperature to obtain the compound of formula 1b.

9. A method for preparing the compound of formula 1c

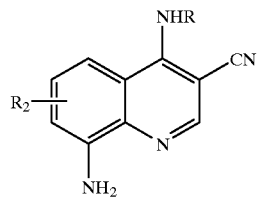

Formula 1c

R is H; C$_{6-14}$ aryl substituted by C$_{1-6}$ alkyl; 5–5 membered heterocyclic group substituted by C$_{1-6}$ alkyl; or —(CH$_2$)$_n$—CHR$_4$R$_5$ wherein n is 0, 1, 2, 3 or 4;

R$_4$ is H; C$_{1-6}$ alkyl; C$_{1-6}$ alkoxy; C$_{6-14}$ aryl unsubstituted or substituted by halogen, C$_{1-6}$ alkyl, C$_{1-6}$ halogenoalkyl, C$_{1-6}$ alkoxy or amino; 5–15 membered heteroaryl; C$_{3-6}$ cycloalkyl; 5–15 membered heterocyclic group; or C$_{6-14}$ aryl fused to 5–15 membered heterocyclic group;

R$_5$ is H; C$_{1-6}$ alkyl; C$_{1-6}$ alkoxy; or C$_{1-6}$ alkoxyalkyl; and

R$_2$ is H; halogen; C$_{1-6}$ alkyl; C$_{1-6}$ alkoxy; C$_{1-6}$ alkoxyalkyl; or C$_{3-6}$ cycloalkyl;

or its pharmaceutically acceptable salt which is characterized by comprising the steps of:

1) reacting the compound of formula 16

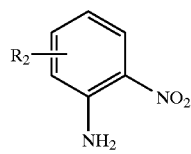

Formula 16 with the compound of formula 17

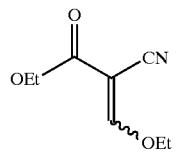

Formula 17 without solvent at 100 to 150 C° with heating or with organic solvent at its boiling point to obtain the compound of formula 18

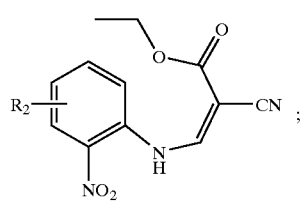

Formula 18

2) cyclizing the compound of formula 18 in organic solvent at 200 C° to the boiling point of the solvent with healing to obtain the compound of formula 19

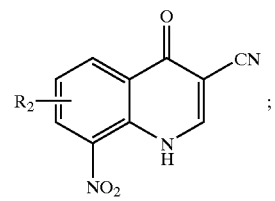

Formula 19

3) reacting the compound of formula 19 with phosphorous oxychloride, phosphorous trichloride or phosphorous pentachloride to obtain the compound of formula 20

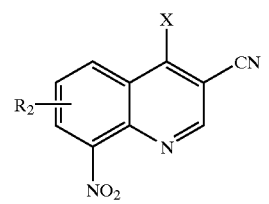

Formula 20 wherein X is halogen, or reacting the compound of formula 19 with sulphonylchloride or phosphorylchloride in organic solvent with the addition of base at −10 C° to ambient temperature to obtain the compound of formula 20 wherein X is sulphonate or phosphonate;

4) reacting the compound of formula 20 with the amine of formula 7

RNH$_2$  Formula 7 in organic solvent at ambient temperature to the boiling poing of the solvent to obtain the compound of formula 21

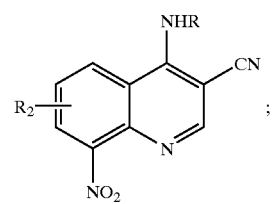

Formula 21

5) reducing the compound of formula 21 with the metal catalyst and hydrogen gas in organic solvent at ambient temperature to obtain the compound of formula 1c.

10. A pharmaceutical composition for treating caspase-associated diseases by inhibiting the activity of caspase-3 which is characterized by comprising a pharmaceutically effective amount of the compound of formula 1 or its pharmaceutically acceptable salt:

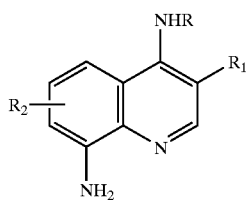

Formula 1 wherein R, R$_1$ and R$_2$ are the same as defined in claim 1.

11. The pharmaceutical composition of claim 10 where the compound of formula 1 is selected from the group consisting of 8-amino-4-[(pyridine-2-ylmethyl)-amino]-quinoline-3-carboxylic acid ethyl ester, 8-amino-4-(3-morpholine-4-yl-propylamino)-quinoline-3-carboxylic acid ethyl ester, 8-amino-4-(3-isopropoxy-propylamino)-quinoline-3-carboxylic acid ethyl ester, 8-amino-4-(2-methoxy-ethylamino)-quinoline-3-carboxylic acid ethyl ester, and their pharmaceutically acceptable salts.

12. The pharmaceutical composition of claim 10 where the caspase-associated disease is selected from the group consisting of Alzheimer's disease, Huntington's disease, Parkinson's disease, ALS, AIDS, stroke, ischemia, traumatic brain injury, spinal cord injury or osteoarthritis.

* * * * *